(12) United States Patent
Ishiwata et al.

(10) Patent No.: US 7,196,101 B2
(45) Date of Patent: Mar. 27, 2007

(54) BIS(5-ARYL-2-PYRIDYL) DERIVATIVES

(75) Inventors: Hiroyuki Ishiwata, Ichikawa (JP); Seiichi Sato, Suginami-ku (JP); Mototsugu Kabeya, Higashimurayama (JP); Soichi Oda, Higashimurayama (JP); Makoto Suda, Higashimurayama (JP); Manabu Shibasaki, Chiba (JP)

(73) Assignee: Kowa Co., Ltd, Nagoya (JP)

( * ) Notice: Subject to any disclaimer, the term of this patent is extended or adjusted under 35 U.S.C. 154(b) by 363 days.

(21) Appl. No.: 10/690,671

(22) Filed: Oct. 23, 2003

(65) Prior Publication Data

US 2005/0101634 A1 May 12, 2005

Related U.S. Application Data

(62) Division of application No. 09/893,698, filed on Jun. 29, 2001, now Pat. No. 6,706,703.

(51) Int. Cl.
  A61P 37/08 (2006.01)
  A61K 31/44 (2006.01)
  C07D 213/00 (2006.01)

(52) U.S. Cl. .................... 514/332; 514/333; 546/256; 546/264

(58) Field of Classification Search ........... 514/332, 514/333; 546/256, 264
See application file for complete search history.

(56) References Cited

FOREIGN PATENT DOCUMENTS

| EP | 0 787 491 | 8/1997 |
|---|---|---|
| JP | 59-167564 | 9/1984 |
| JP | 1-106818 | 4/1989 |
| JP | 7-017506 | 3/1995 |
| JP | 8-092216 | 4/1996 |
| JP | 8-109177 | 4/1996 |
| JP | 10-324631 | 12/1998 |
| JP | 11-269192 | 10/1999 |
| WO | WO 96/11682 | 4/1996 |
| WO | WO 98/04508 | 2/1998 |
| WO | WO 98/07702 | 2/1998 |
| WO | WO 98/16497 | 4/1998 |
| WO | WO 99/19291 | 4/1999 |
| WO | WO 99/35140 | 7/1999 |
| WO | WO 99/38829 | 8/1999 |
| WO | WO 99/42446 | 8/1999 |
| WO | WO 00/05198 | 2/2000 |

OTHER PUBLICATIONS

Robert B. Fick, Jr., Current Opinion in Pulmonary Medicine, vol. 5, pp. 76-80, "Anti-IgE as Novel Therapy for the Treatment of Asthma", 1999.

Farhad Imani, Emerging Therapeutic Targets, vol. 3, No. 2, pp. 229-240, "Emerging Therapeutic Targets in Asthma and Allergy: Modulation of IgE", 1999.

Henry Milgrom, et al., The New England Journal of Medicine, vol. 341, No. 26, pp. 1966-1973, "Treatment of Allergic Asthma With Monoclonal Anti-IgE Antibody", Dec. 23, 1999.

Naosuke Matsuura, et al., Jpn. Pharmacol. Ther., vol. 22, No. 3, pp. 1369-1383, "An Immunopharmacological Study of (±)—[2- [4-(3-Ethoxy-2-Hydroxypropoxy) Phenylcarbamoyl] Ethyl] Dimethylsulfonium P-Toluenesulfonate (Suplatast Tosilate, IPD-1151T)", 1994.

U.S. Appl. No. 10/690,671, filed Oct. 23, 2003, Ishiwata et al.
U.S. Appl. No. 09/893,680, filed Jun. 29, 2001, Ishiwata et al.

Primary Examiner—Brenda Coleman
(74) Attorney, Agent, or Firm—Oblon, Spivak, McClelland, Maier & Neustadt, P.C.

(57) ABSTRACT

A bis(5-aryl-2-pyridyl) compound represented by formula (1) or a salt thereof:

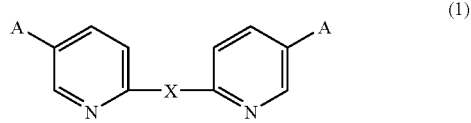

wherein A is a substituted or unsubstituted aromatic hydrocarbyl group or a substituted or unsubstituted aromatic heterocyclic group, and X is a group selected from the group consisting of moieties having formulas (2) to (5):

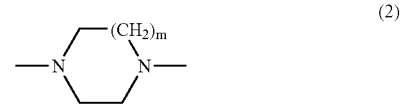

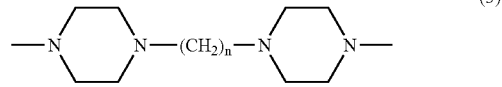

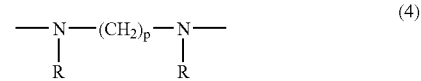

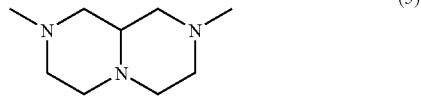

wherein, in formula (2), m is an integer of 1 or 2; in formula (3), n is an integer of 1 to 6; and in formula (4), R is hydrogen or a lower alkyl group and p is an integer of 1 to 6.

10 Claims, No Drawings

BIS(5-ARYL-2-PYRIDYL) DERIVATIVES

This application is a divisional of U.S. Ser. No. 09/893,698 filed Jun. 29, 2001, now U.S. Pat. No. 6,706,703.

BACKGROUND OF THE INVENTION

1. Field of the Invention

The present invention relates to bis(5-aryl-2-pyridyl) derivatives or salts thereof, and also to medicinal compositions which comprise the bis(5-aryl-2-pyridyl) derivatives or salts-thereof as active ingredients and are useful for the prevention or treatment of allergic immune diseases.

2. Discussion of the Background

IgE, a class of immunoglobulin (Ig), is an allergen-specific molecule produced by IgE producing cells differentiated from B cells, when triggered by contact of immunocytes with an allergen in the body.

IgE is produced in an organ targeted by allergy, and binds to a receptor on-surfaces of mast cells which are the principal effector cells in an allergic reaction or basophils (sensitized state). From the mast cells, which are stimulated as a result of intrusion of the allergen into the body after sensitization and the accompanying reaction with the specific IgE, allergic chemical mediators such as histamine, leucotrienes, prostaglandins and PAF, and tissue destructive enzymes such as tryptase are released thereby provoking the immediate responses of an allergic reaction such as increased vasopermeability, smooth muscle constriction or vasodilation. From the stimulated mast cells, cytokines, such as IL-4, which directly activate other immune system cells are also secreted. As a result, eosinophils, basophils or the like infiltrate tissues, and allergic chemical mediators or tissue destructive proteins such as MBP, which are secreted by these inflammatory cells, induces late responses of an allergic reaction to protract and worsen an allergic symptom.

As can be appreciated from the foregoing remarks, an abnormality in IgE production is highly relevant to various allergic immune diseases such as asthma, atopic dermatitis, allergic rhinitis, inflammatory bowel disease, contact dermatitis and allergic ophthalmopathy. It is known that inhibition of IgE production makes it possible to prevent and/or treat these diseases (Emerging Therapeutic Targets In Asthma And Allergy: Modulation Of IgE, *Emerging Therapeutic Targets*, 3, 229–240 (1990); Anti-IgE As Novel Therapy For The Treatment Of Asthma, *Curr. Opin. Plum. Med.*, 5, 76–80 (1999); Treatment Of Allergic, Asthma With Monoclonal Anti-IgE Antibody, *N. Eng. J. Med.*, 341, 1966–1973 (1999); Anti-IgE Antibody Therapy For Asthma, *N. Eng. J. Med.*, 341, 2006–2008 (1999)).

From the foregoing, IgE is believed to be a substance which takes part in the manifestation of an allergic disease at the onset of the disease. With the objective of developing antiallergic agents, some small molecules with IgE antibody production inhibiting activity have been found and reported to date (WO 98/04058, WO 98/07702, WO 98/16497, JP 10-324631A, WO 99/19291, WO 99/35140, WO 99/38829, WO 99/42446, JP 11-269192A, WO 00/05198, "Yakuri to Chiryo (Basic Pharmacology & Therapeutic)" 22(3), 1369 (1994), JP 1-106818A, JP 7-17506B, JP 8-92216A, JP 8-109177A, WO 96/11682, JP 59-167564A). These compounds, however, involve problems such as low solubility in water, and therefore they are not entirely satisfactory agents in the therapeutic treatment of allergic disease.

SUMMARY OF THE INVENTION

Accordingly, one object of the present invention is to provide a compound having excellent IgE antibody production inhibiting activity and also a medicinal composition comprising the compound as an active ingredient.

Briefly, this object and other objects of the present invention as hereinafter will become more readily apparent can be attained by a bis(5-aryl-2-pyridyl) compound having the following formula (1) or a salt thereof:

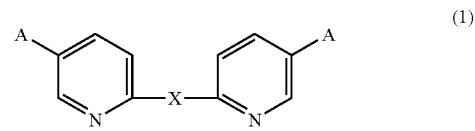

wherein A is a substituted or unsubstituted aromatic hydrocarbon group or a substituted or unsubstituted aromatic heterocyclic group, and X is a substituent selected from the group consisting of formulas (2) to (5):

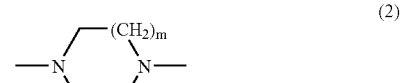

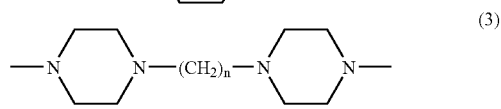

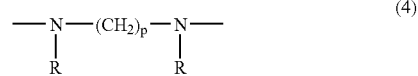

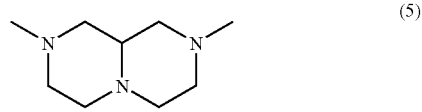

wherein, in formula (2), m is an integer of 1 or 2; in formula (3), n is an integer of 1 to 6; and in formula (4), R is hydrogen or lower alkyl and p is an integer of 1 to 6.

Another aspect of the present invention is a medicinal composition comprising the active bis(5-aryl-2-pyridyl) compound or the salt thereof of the invention.

Still another aspect of the present invention is a medicinal composition comprising the active bis(5-aryl-2-pyridyl) compound or the salt thereof in combination with a pharmacologically acceptable carrier.

Yet another aspect of the present invention is a method of treating a subject for an allergic immune disease by administering the bis(5-aryl-2-pyridyl) derivative or the salt thereof of the invention to a subject.

DETAILED DESCRIPTION OF THE PREFERRED EMBODIMENTS

As a result of the investigative work by the present inventors, the present compound, has been found to exhibit an excellent IgE antibody production inhibiting activity and also good solubility in later, and therefore are useful in the treatment of allergic immune diseases.

Illustrative of the lower alkyl moiety in "lower alkyl groups", "halogeno(lower alkyl) groups", "hydroxy(lower alkyl) groups", "lower alkoxy(lower alkyl) groups", "lower alkoxy groups", "(lower alkylthio groups", "(lower alkyl) amino groups", "(lower alkyl)sufonylamino groups", "(lower alkoxy)carbonyl groups" and "lower alkanoyl groups" as used herein are linear, branched or cyclic alkyl groups having 1 to 6 carbon atoms. Suitable examples of lower alkyl groups include methyl, ethyl, n-propyl, isopropyl, n-butyl, isobutyl, sec-butyl, tert-butyl, pentyl, hexyl, cyclopropyl, and cyclohexyl. Further, suitable halogen atoms include fluorine, chlorine, bromine and iodine.

In formula (1), the aromatic hydrocarbon group represented by A preferably has 6 to 14 carbon atoms, with phenyl or naphthyl being more preferred and phenyl being particularly preferred. Preferred examples of the aromatic heterocyclic group include 5- to 10-membered heterocyclic groups each of which contains one or two nitrogen, oxygen or sulfur atoms, with pyridyl, thienyl, furyl, benzofuryl and benzothienyl groups being more preferred. These groups may contain 1 to 3 substituents. Suitable examples of such substituents include lower alkyl groups, halogeno(lower alkyl) groups, hydroxy(lower alkyl) groups, lower alkoxy (lower alkyl) groups, lower alkoxy groups, halogen atoms, hydroxy group, cyano group, (lower alkyl)thio groups, amino group, mono- or di-(lower alkyl)amino groups, (lower alkyl)sufonylamino groups, formyl group, carboxyl group, (lower alkoxy)carbonyl groups, lower alkanoyl groups, pyrrolidinyl group and alkylenedioxy groups.

Preferred specific examples of these substituents include methyl, t-butyl, trifluoromethyl, hydroxymethyl, methoxymethyl, methoxy, ethoxy, isopropoxy, fluoro, chloro, hydroxy, cyano, methylthio, amino, dimethylamino, methanesulfonylamino, pyrrolidinyl, formyl, carboxyl, methoxycarbonyl, ethoxycarbonyl, acetyl, and methylenedioxy.

Among the groups represented by X, preferred is the group of formula (3) in which n is an integer of 2 to 4 and the group of formula (4) in which p is an integer of 2 to 4.

Preferred specific examples of the bis(5-aryl-2-pyridyl) derivative (1) of the present invention include 1,4-bis[5-(3,4,5-trimethoxyphenyl)-2-pyridyl]hexahydro-1,4-diazepine dimethanesulfonate, 1,4-bis[5-(4-amino-3,5-dimethoxyphenyl)-2-pyridyl]hexahydro-1,4-diazepine tetrahydrochloride, 1,4-bis[5-(4-dimethylamino-3,5-dimethoxyphenyl)-2-pyridyl]hexahydro-1,4-diazepine, 1,3-bis[4-[5-(3,4,5-trimethoxyphenyl)-2-pyridyl]-1-piperazinyl]propane, and N,N'-bis[5-(3,4,5-trimethoxyphenyl)-2-pyridyl]-N,N'-dimethylethylenediamine dimethanesulfonate.

Compound (1) of the present invention can be produced, for example, by the following sequence of reaction steps, although no particular limitation is imposed on the method of synthesis employed.

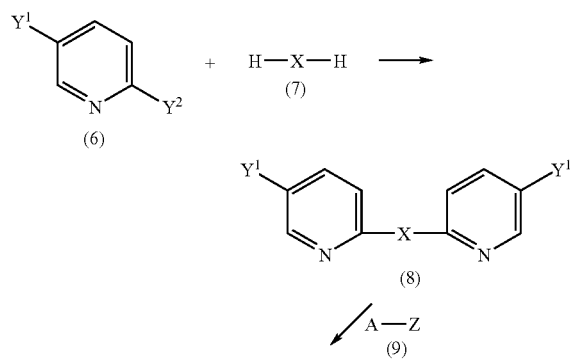

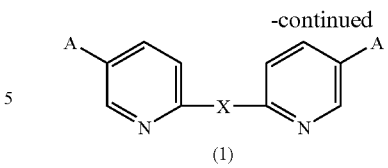

wherein A and X have the same meanings as defined above, $Y^1$ and $Y^2$ each are halogen or $-OSO_2(C_qF_{2q+1})$ in which q is 0 or an integer of 1 to 4, and Z is dihydroxyboron, di(lower alkoxy)boron, di(lower alkyl)boron, dihalo(lower alkyl)silicon, halogenated zinc, tri(lower alkyl)tin, halogenated magnesium or the like.

Specifically, compound (1) of the present invention can be produced by reacting compound (6) with compound (7) in the absence of a solvent or in a solvent optionally in the presence of a base to prepare compound (8) and then reacting compound (8) with compound (9).

Suitable examples of the solvent employed in the reaction (condensation reaction) between compound (6) and compound (7) include toluene, tetrahydrofuran, dioxane and dimethylformamide, whereas examples of the base employable in the reaction include potassium carbonate and sodium hydride. The reaction is preferably conducted at room temperature to 200° C. for 0.5 to 100 hours, notably at 80 to 120° C. for 2 to 15 hours.

To prepare compound (1) of the present invention, the reaction (cross-coupling reaction) between compound (8) and compound (9) can be conducted by adding compound (9) and a catalyst to a solution or suspension of compound (8) and allowing compound (8) to react with compound (9) optionally in the presence of a ligand and a base (Metal-Catalyzed Cross-Coupling Reactions; Diederich, F., Stang, P. J., Eds.; Wiley-VHC: Weinheim (1998). Stanforth, S. P., *Tetrahedron*, 54, 263–303 (1998)).

Suitable examples of a solvent employable in the above reaction include benzene, toluene, xylene, diethyl ether, tetrahydrofuran, dimtethoxyethane, dioxane, acetonitrile, dimethylformamide, N-methylpiperidone, methanol, ethanol, and water. Suitable examples of the catalyst include tetrakis(triphenylphosphine)palladium(0), tris(bisbenzylideneacetone)dipalladium(0), palladium(II) acetate, palladium (II) chloride dichlorobis(triphenylphosphine)palladium(II), dichloro[1,2-bis(diphenylphosphino)ethane]palladium(II), dichloro[1,4-bis(diphenylphosphino)butane]palladium(II), dichloro[1,1'-bis(diphenylphosphino)ferrocene]palladium (II), tetrakis(triphenylphosphine)nickel(0) and bis(acetylacetonato)nickel(II).

Suitable examples of the ligand, on the other hand, include tri(t-butyl)phosphine, triphenylphosphine, tri(o-tolyl)phosphine, tri(2-furyl)phosphine, 2,2'-bis(diphenylphosphino)-1,1'-binaphthyl, 1,2-bis(diphenylphosphino)ethane, 1,3-bis(diphenylphosphino)propane, 1,4-bis (diphenylphosphino)butane, and 1,1'-bis (diphenylphosphino)ferrocene. Suitable examples of the base include sodium acetate, potassium carbonate, sodium carbonate, sodium hydrogencarbonate; potassium phosphate, sodium hydroxide, potassium hydroxide, barium hydroxide, sodium methoxide, sodium ethoxide, cesium fluoride, tributylammonium fluoride, and triethylamine.

As to the reaction conditions, the reaction may be conducted at room temperature up to a temperature of 150° C. for 0.5 to 100 hours. It is, however, preferred to follow the details of the reaction reported by Suzuki et al, (Miyaura, N.;

Suzuki, A., *Chem. Rev.*, 95, 2457–2483 (1995)). Here, compound (9) is employed in which Z is dihydroxyboron and the reaction is conducted under conditions of tetrakis (triphenylphosphine)palladium(0)/potassium carbonate (or sodium carbonate)/water-methanol(or ethanol)-toluene/60 to 100° C./0.5 to 3 hours; or a compound (9) in which Z is di(lower alkoxy)boron is reacted under conditions of dichloro[1,1'-bis(diphenylphosphino)ferrocene]palladium (II)/1,1'-bis(diphenylphosphino)ferrocene/sodium carbonate/water-dimethylformamide/60 to 100° C./0.5 to 3 hours.

The compounds obtained in the above reactions, respectively, can be isolated and purified by subjecting them to purification procedures commonly employed in synthetic organic chemistry, for example, filtration, extraction, washing, drying, concentration, recrystallization, one or more of various types of chromatography, and the like. Further, the intermediate can be provided for use in the next reaction without the need of specifically purifying the compound.

In addition, the product and intermediate may also be obtained in the form of solvates with reaction solvents, recrystallization solvents or the like, especially as hydrates. Further, compound (1) of the present invention may include various isomers depending on the kinds and combination of substituents in the molecule. It is to be noted that the present invention encompasses all of such isomers.

Compound (1), obtained as described above, can be converted into an acid addition salt or a basic salt by a method known per se in the art. No particular limitation is imposed on such salts insofar as they are pharmacologically acceptable salts. When compound (1) is a basic compound, examples of a pharmacologically acceptable salt thereof include mineral acid salts such as the hydrochloride, sulfate and nitrate; and organic acid salts such as the methanesulfonate, acetate, oxalate and citrate. When compound (1) is an acidic compound, on the other hand, examples of pharmacologically acceptable salts thereof include alkali metal salts such as the sodium and potassium salts; alkaline earth metal salts such as the calcium and magnesium salts; and organic base salts such as the pyridine, picoline and triethylamine salts.

The bis (5-aryl-2-pyridyl) compound (1) of the present invention has excellent IgE antibody production inhibiting activity as is demonstrated in tests described below, as well as IL-4 production inhibiting activity and IL-5 production inhibiting activity. The compound is useful as medicinal agent for the prevention or treatment of various allergic diseases, for example, asthma, atopic dermatitis, allergic rhinitis, inflammatory bowel disease, contact dermatitis and allergic ophthalmopathy, and also as an IgE antibody production inhibitor.

The medicinal composition of the present invention comprises, as an active ingredient, the bis(5-aryl-2-pyridyl) compound or a salt thereof. By adding pharmacologically acceptable, inorganic or organic carriers, the bis(5-aryl-2-pyridyl) compound or salt thereof can be formulated into medicinal compositions, for example, various oral preparations or parenteral preparations such as solid, semi-solid or liquid preparations by methods known per se in the art.

Illustrative of preparations for oral administration are tablets, pills, granules, soft or hard capsules, triturates, subtilized granules, powders, emulsions, syrups, pellets, and elixirs. On the other hand, illustrative preparations for parenteral administration include injectable formulations, drips, infusions, ointments, lotions, tonics, sprays, suspensions, medicinal oils, emulsions, suppositories, and instillation.

To formulate such preparations, methods known per se in the art can be followed. The active ingredient of the present invention can be used in combination with pharmacologically acceptable surfactants, excipients, coloring agents, flavoring agents, preservatives, stabilizers, buffering agents, suspending agents, isotonicities and the like as needed.

The dosage of the therapeutic agent of the present invention varies inter alia depending on the compound, the disease to be treated or prevented, the method of administration, the period of treatment, and, the age, sex and weight of the patient. Nonetheless, it is preferred to administer the medicine at a daily dosage ranging from 0.01 to 1,000 mg/kg weight in terms of the compound represented by formula (1). This dosage can be administered at once or in several portions, for example, 2 to 6 portions in a day.

Having now generally described this invention, a further understanding can be obtained by reference to certain specific examples which are provided herein for purposes of illustration only and are not intended to be limiting unless otherwise specified.

REFERENCE EXAMPLE 1

1,4-Bis(5-bromo-2-pyridyl)hexahydro-1,4-diazepine

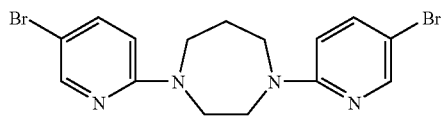

To a solution of hexahydro-1,4-diazepine (2.84 g, 28.4 mmol) in dimethylformamide (14 mL) were added 2,5-dibromopyridine (16.23 g, 68.5 mmol) and potassium carbonate powdered in a mortar (8.00 g, 57.9 mmol), and the resultant mixture was stirred at 120° for 15 hours. Water was added to the reaction mixture, and the mixture was extracted with chloroform. The organic layer was dried over anhydrous sodium sulfate and concentrated under reduced pressure. The residue was purified by column chromatography on silica gel to yield crude crystals of the title compound (7.67 g, yield: 66%). The crude crystals were recrystallized from chloroform-hexane to give colorless fine needles (melting point: 178.0–181.0° C.

REFERENCE EXAMPLE 2

3,5-Dimethoxyphenylboronic Acid

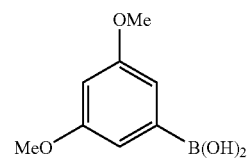

Under argon, to anhydrous tetrahydrofuran (9.0 mL) stirred in a dry ice-methanol bath was gradually added a 1.57 M solution of n-butyllithium in hexane (3.9 mL, 5.9 mmol), followed by the dropwise addition of a solution of 3,5-dimethoxyiodobenzene (713.0 mg, 2.70 mmol) in anhydrous tetrahydrofuran (5.0 mL). After the mixture was stirred for 20 minutes in the dry ice-methanol bath, triisopropyl borate (0.75 mL, 3.2 mmol) was added and the mixture was additionally stirred for 20 minutes. The reaction mixture was stirred at room temperature for 1 hour and concentrated under reduced pressure, then a 1.0 M aqueous sodium hydroxide (7.0 mL) was added to the residue. The resulting aqueous solution was washed with chloroform, acidified by adding concentrated hydrochloric acid, and extracted with chloroform. The organic layer was washed with brine, dried over anhydrous sodium sulfate, and then concentrated under reduced pressure. The residue was recrystallized from chloroform-hexane to yield the title compound as a colorless crystalline powder (melting point: 159.0–161.0° C.)(367.0 mg, yield: 91%).

REFERENCE EXAMPLE 3

3,5-Diisopropoxyphenyl trifluoromethanesulfonate

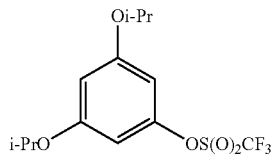

To a solution of 3,5-diisopropoxyphenol (*J. Chem. Soc. Perkin Trans.*, 1, 17, 2939–2942 (1998)). (170.0 mg, 0.810 mmol) in methylene chloride (4.5 mL) was added N,N-diisopropylethylamine (195.0 mg, 1.50 mmol). The resulting solution was cooled in a dry ice-methanol bath, and trifluoromethanesulfonic anhydride (367.0 mg, 1.30 mmol) was added dropwise over approximately 10 minutes., After stirring for 3 hours, brine was added to the reaction mixture, and the mixture was extracted with chloroform. The organic layer was dried over anhydrous sodium sulfate and concentrated under reduced pressure. The residue was purified by column chromatography on silica gel to yield the title compound as a pale yellow oil (261.0 mg, yield: 94%).

REFERENCE EXAMPLE 4

3,5-Bis(methoxymethyl)phenyl trifluoromethanesulfonate

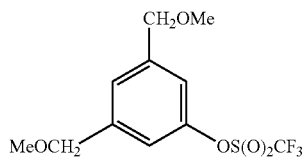

To an ice-cold stirred solution of dimethyl 5-hydroxyisophthalate (*J. Org. Chem.*, 65, 5360–5370 (2000)). (1.25 g, 5.95 mmol) in anhydrous dimethylformamide (10 mL) were added imidazole (0.83 g, 12.2 mmol) and t-butylchlorodiphenylsilane (2.2 mL, 8.5 mmol). After stirring in ice for 15 minutes and at room temperature for 2 hours, water was added and the mixture was extracted with benzene-hexane (1:1). The organic layer was dried over anhydrous sodium sulfate and concentrated under reduced pressure to afford an oil (3.40 g) containing dimethyl 5-(t-butyldiphenylsiloxy) isophthalate.

Lithium aluminum hydride (1.00 g, 26.4 mmol) was added to an ice-cold solution of the oil (3.22 g) obtained by the above-described procedure, in anhydrous tetrahydrofuran (35 mL), and the mixture was stirred for 20 minutes. Methanol (7.0 mL, 170 mmol) was added to the reaction mixture, and the ice bath was removed. Water (7.0 mL), diethyl ether (150 mL), and anhydrous magnesium sulfate (30 g) were added, and the mixture was stirred at room temperature for 3 hours, then insoluble materials were removed by filtration through Celite. The residue was flashed with chloroform, then the filtrate and the washing were combined and concentrated under reduced pressure. The residue was recrystallized from diethyl ether-hexane to yield 1-t-butylphenylsiloxy-3,5-bis(hydroxymethyl)benzene as colorless needles (melting point: 132.0–133.0° C.) (1.76 g, yield: 75% based on dimethyl 5-hyroxyisophthalate).

Methyl iodide (0.80 mL, 13 mmol) and a 50% dispersion of sodium hydride in mineral oil (156.5 mg, 3.26 mmol) were added to an ice-cold solution of 1-t-butyldiphyenylsiloxy-3,5-bis(hydroxymethyl)benzene (501.3 mg, 1.28 mmol) in dimethylformamide (5.0 mL), and the mixture was stirred for 1 hour. Water was added to the reaction mixture, and the mixture was extracted with benzene-hexane (1:1). The organic layer was dried over anhydrous sodium sulfate and concentrated under reduced pressure to afford an oil (0.60 g) containing 1-t-butyldiphenylsiloxy-3,5-di(methoxymethyl)benzene.

A 1.0 M solution of tetrabutylammonium fluoride in tetrahydrofuran (2.0 mL, 2.0 mmol) was added to an ice-cold solution of the oil (0.60 g) obtained by the above-described procedure in tetrahydrofuran (8.0 mL), and the mixture was stirred for 15 minutes. An approx. 20% aqueous ammonium chloride was added, and the mixture was extracted with diethyl ether. The organic layer was dried over anhydrous sodium sulfate and concentrated under reduced pressure. The residue was purified by column chromatography on silica gel to yield 3,5-bis(methoxymethyl)phenol as a colorless oil [219.8 mg, yield: 94% based on 1-t-butyldiphenylsiloxy-3,5-bis(hydroxymethyl)benzene].

By a similar procedure as in Reference Example 3, the title compound was obtained as a colorless oil (343.9 mg, yield: 93%) from 3,5-bis(methoxymethyl)phenol (215.4 mg, 1.18 mmol).

REFERENCE EXAMPLE 5

3,4,5-Triethoxyphenylboronic Acid

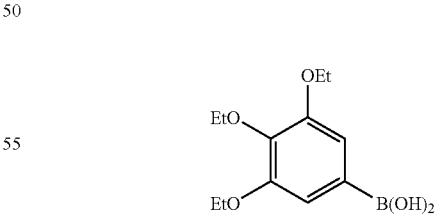

A solution of 3,4,5-triethoxybenzoic acid (20.0 g, 78.7 mmol) in acetic acid (68 mL) was stirred at 15° C., and concentrated nitric acid (d 1.38)(34 mL, 750 mmol) was added. After stirring at room temperature for 1 hour, the reaction mixture was poured into ice water and the mixture was extracted with ethyl acetate. The organic layer was washed with a saturated aqueous sodium hydrogencarbonate and brine, dried over anhydrous sodium sulfate, and concentrated under reduced pressure. The residue was purified by column chromatography on silica gel to yield 3,4,5-triethoxy-1-nitrobenzene as a colorless oil (12.9 g, yield: 64%).

To a solution of 3,4,5-triethoxy-1-nitrobenzene (12.9 g, 50.5 mmol) in methanol (445 mL) were added 10% palladium on charcoal (6.7 g) and ammonium formate (16.2 g, 253 mmol), and the mixture was stirred at 70° C. for 1 hour. Insoluble materials were removed by filtration through Celite, and the filtrate was concentrated under reduced pressure. A solution of the residue in chloroform was washed with water and brine, dried over anhydrous sodium sulfate, and concentrated under reduced pressure to afford an oil (10.5 g) containing 3,4,5-triethoxyaniline.

The oil (9.5 g, approx. 42.2 mmol) obtained by the above procedure was suspended in water (200 mL). Concentrated sulfuric acid (7.3 mL, 88 mmol) was added to the ice-cold suspension to provide a homogeneous solution. A solution of sodium nitrite (3.10 g, 44.0 mmol) in water (10 mL) was added dropwise to the ice-cold solution over approximately 10 minutes, and the solution was stirred for 15 minutes, followed by the addition of a solution of potassium iodide (7.70 g, 46.0 mmol) in water (10 mL). The reaction mixture was stirred at room temperature for 1 hour and at 50° C. for 15 minutes, and extracted with ethyl acetate. The organic layer was bashed with brine, dried over anhydrous sodium sulfate, and concentrated under reduced pressure. The residue was purified by column chromatography silica gel to yield 3,4,5-triethoxy-1-iodobenzene as pale yellow needles (melting point: 44.0–46.0° C.)(11.60 g, yield: 75%).

By a similar procedure as in Reference Example 2, crude crystals were obtained from 3,4,5-triethoxy-1-iodobenzene (5.00 g, 14.9 mmol). The crude crystals were recrystallized from chloroform-hexane to yield the title compound as colorless needles (melting point. 167.0–168.0° C.) (1.80 g, yield: 48%).

REFERENCE EXAMPLE 6

3,5-Diisopropoxy-4-methoxyphenylboronic Acid

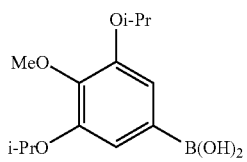

To a solution of methyl 3,5-dihydroxy-4-methoxybenzoate (*Ann. Chem.*, 544, 62–71 (1940)). (4.40 g, 22.2 mmol) in dimethylformamide (44.0 mL) were added potassium carbonate (10.20 g, 73.8 mmol) and isopropyl iodide (19.66 g, 115 mmol). After stirring at 70° C. for 3 hours, water was added to the reaction mixture. The resulting mixture was extracted with diethyl ether. The organic layer vas dried over anhydrous sodium sulfate and then concentrated under reduced pressure. The residue was purified by column chromatography on silica gel to yield methyl 3,5-diisopropoxy-4-methoxybenzoate as a pale yellow oil (4.16 g, yield: 66%).

To a solution of methyl 3,5-diisopropoxy-4-methoxybenzoate (4.16 g, 14.7 mmol) in methanol(20 mL) a 5.0 M aqueous sodium hydroxide (20.0 mL, 100 mmol) was added. After stirring at 80° C. for 3 hours, the reaction mixture was concentrated under reduced pressure to remove the methanol. The residue was acidified by the addition of concentrated hydrochloric acid and extracted with chloroform. The organic layer was washed with brine, dried over anhydrous sodium sulfate, and concentrated under reduced pressure to yield an oil (4.00 g) containing 3,5-diisopropoxy-4-methoxybenzoic acid.

The following synthetic procedure was carried out according to the procedure of Reference Example 5. From the oil (3.70 g) obtained by the above-described procedure, 3,5-diisopropoxy-4-methoxy-1-nitrobenzene (1.70 g) was obtained as a pale yellow oil (yield: 46% based on methyl 3,5-diisopropoxy-4-methoxybenzoate). From 3,5-diisopropoxy-4-methoxy-1-nitrobenzene (1.70 g, 6.30 mmol), 1-iodo-3,5-diisopropoxy-4-methoxybenzene was obtained as a pale yellow oil (1.45 g, yield: 66%). From 1-iodo-3,5-diisopropoxy-4-methoxybenzene. (700.0 mg, 2.17 mmol), the title compound was obtained as a colorless crystalline powder (melting point: 159.0–161.0° C.) (367.0 mg, yield: 70%).

REFERENCE EXAMPLE 7

3-Methoxy-4,5-methylenedioxyphenylboronic Acid

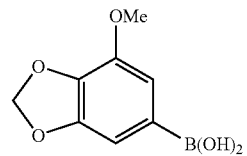

To a solution of 3-hydroxy-4,5-methylenedioxybenzoic acid (*Liebigs Ann. Chem.*, 361–364 (1994)) (3.90 g, 20.0 mmol) in dimethylformamide (20.0 mL) were added potassium carbonate (2.80 g, 20.0 mmol) and methyl iodide (4.30 g, 30.0 mmol), and the mixture was stirred at 50° C. for 1 hour. Water was added to the reaction mixture, and the mixture was extracted with diethyl ether. The organic layer was dried over anhydrous sodium sulfate and concentrated under reduced pressure. The residue was purified by column chromatography on silica gel to yield methyl 3-methoxy-4,5-methylenedioxybenzoate as a colorless viscous oil (4.30 g, yield: 98%).

Synthesis of the title compound from methyl 3-methoxy-4,5-methylenedioxybenzoate was carried out by applying the synthetic procedure of 3,5-diisdpropoxy-4-methoxyphenylboronic acid from methyl 3,5-diisopropoxy-4-methoxybenzoate in Reference Example 6. From methyl 3-methoxy-4,5-methylenedioxybenzoate (4.30 g, 20.5 mmol), 3-methoxy-4,5-methylenedioxybenzoic acid (3.00 g) was obtained as colorless prisms (melting point: 215.0–216.0° C.) (yield: 71%). From 3-methoxy-4,5-methylenedioxybenzoic acid (2.50 g, 12.7 mmol), 3-methoxy-4,5-methylenedioxy-1-nitrobenzene was obtained as a pale yellow amorphous powder (1.26 g, yield: 50%). From 3-methoxy-4,5-methylenedioxy-1-nitrobenzene (1.26 g, 16.4 mmol), 1-iodo-3-methoxy-4,5-methylenedioxybenzene was obtained as pale yellow needles (melting point: 71.0–72.0° C.) (1.08 g, yield: 61%). From 1-iodo-3-methoxy-4,5-methylenedioxybenzene (750.0 mg, 2.70 mmol), the title compound was obtained as a colorless crystalline powder (melting point: 279.0–281.0° C.) (347.0 mg, yield: 66%).

REFERENCE EXAMPLE 8

4-Benzyloxy-3,5-dimethoxyphenylboronic Acid

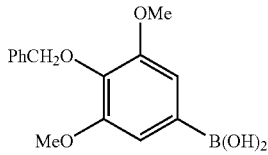

To a solution of methyl syringate (6.00 g, 28.3 mmol) in dimethylformamide (61.0 mL) were added potassium carbonate (2.80 g, 20.3 mmol) and benzyl bromide (5.80 g, 33.9 mmol), and the resulting mixture was stirred at 50° C. for 2 hours. After cooling, water was added, and the mixture was extracted with diethyl ether. The organic layer was washed with brine, dried over anhydrous sodium sulfate, and concentrated under reduced pressure to yield an oil (7.90 g) containing methyl 4-benzyloxy-3,5-dimethoxybenzoate.

To a solution of the oil (7.90 g) obtained by the above-described procedure in methanol (40 mL) was added a 5.0 M aqueous sodium hydroxide (40 mL, 200 mmol). After stirring at 80° C. for 30 minutes, the reaction mixture was concentrated under reduced pressure to remove the methanol. The residue was acidified by the addition of concentrated hydrochloric acid, and extracted with chloroform. The organic layer was washed with brine, dried over anhydrous sodium sulfate, and concentrated under reduced pressure to afford an oil (6.40 g) containing 4-benzyloxy-3,5-dimethoxybenzoic acid.

To a solution of the oil (6.40 g) obtained by the above-described procedure in t-butyl alcohol (96 mL) were added triethylamine (2.43 g, 23.6 mmol) and diphenylphosphoryl azide (6.40 g, 23.6 mmol). After stirring at 100° C. for 2 hours, the reaction mixture was concentrated under reduced pressure. A solution of the residue in ethyl acetate was washed with a saturated aqueous sodium hydrogencarbonate and brine, dried over anhydrous sodium sulfate, and concentrated under reduced pressure. The residue was purified by column chromatography on silica gel to yield 4-benzyloxy-N-t-butoxycarbonyl-3,5-dimethoxyaniline as a colorless oil (4.56 g, yield: 44% based on methyl syringate).

To a solution of 4-benzyloxy-N-t-butoxycarbonyl-3,5-dimethoxyaniline (590.0 mg, 1.64 mmol) in methanol (2.0 mL) was added a 4.0 M solution of hydrogen chloride in ethyl acetate (2.0 mL, 8.0 mmol), and the mixture was stirred at 50° C. for 1 hour. The reaction mixture was concentrated under reduced pressure, and an 8.0 M aqueous sodium hydroxide (1.5 mL, 12 mmol) was added to the residue, then the mixture was extracted with chloroform. The organic layer was washed with brine, dried over anhydrous sodium sulfate, and concentrated under reduced pressure to yield an oil (426.0 mg) containing 4-benzyloxy-3, 5-dimethoxyaniline.

Synthesis of the title compound from the oil obtained by the above-described procedure was carried out by applying the synthetic procedure of 3,4,5-triethoxyphenylboronic acid from the oil containing 3,4,5-triethoxyaniline in Reference Example 5. From the oil (426.0 mg, approximately 1.64 mmol) obtained by the above-described procedure, 4-benzyloxy-1-iodo-3,5-dimethoxybenzene was obtained as a colorless oil (447.0 mg, yield: 73% based on 4-benzyloxy-N-t-butoxycarbonyl-3,5-dimethoxyaniline). From 4-benzyloxy-0.1-iodo-3,5-dimethoxybenzene (447.0 mg, 1.21 mmol), the title compound was obtained as a colorless crystalline powder (melting point: 180.0–183.0° C.) (87.0 mg, yield: 25%).

REFERENCE EXAMPLE 9

3,5-Dimethoxy-4-methylthiophenylboronic Acid

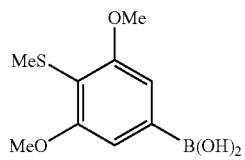

To a solution of 4-bromo-3,5-dimethoxybenzoic acid (*Acta Chem. Scand.*, 2, 34–41, (1948)) (22.6 g, 86.6 mmol) in methylene chloride (400 mL) was added dimethylformamide (1.5 mL, 19.4 mmol). Oxalyl chloride (13.0 g, 102.0 mmol) was gradually added to the ice-cold solution, and the mixture was stirred at room temperature for 1 hour and 30 minutes. The reaction mixture was concentrated under reduced pressure to yield crude crystals of 4-bromo-3,5-dimethoxybenzoyl chloride. To an ice-cold solution of 2-amino-2-methylpropanol (8.40 g, 94.2 mmol) in methylene chloride (100 mL) were added N,N-diisopropylethylamine (16.6 mL, 95.3 mmol) and a solution of the crude 4-bromo-3,5-dimethoxybenzoyl chloride in methylene chloride (200 mL). After the mixture was stirred at room temperature for 10 minutes, the mixture was washed successively with water, 8.0 M hydrochloric acid, a saturated aqueous sodium hydrogencarbonate and brine, dried over anhydrous sodium sulfate, and concentrated under reduced pressure. Thionyl chloride (47.5 mL, 651.0 mmol) was added to the residue, and the mixture was stirred at room temperature for 10 minutes. To the reaction mixture were added ice water and a 2.5 M aqueous sodium hydroxide (600 mL, 1500 mmol), and the mixture was extracted with diethyl ether. The organic layer was washed with brine, dried over anhydrous sodium sulfate, and concentrated under reduced pressure. The residue was recrystallized form diethyl ether-hexane to yield 2-(4-bromo-3,5-dimethoxyphenyl)-4,4-dimethyl-2-oxazoline as colorless fine needles (melting point: 172.5–174.5° C.) (20.9 g, yield: 77%).

Under argon, to a solution of 2-(4-bromo-3,5-dimethoxyphenyl)-4,4-dimethyl-2-oxazoline (51.43 g, 0.164 mmol) in anhydrous tetrahydrofuran (1000 mL) stirred in a dry ice-methanol bath were added dropwise N,N,N',N'-tetramethylethylenediamine (30.0 mL, 0.199 mol) and a 1.59 M solution of n-butyl lithium in hexane (134.0 mL, 0.213 mol). After stirring for 10 minutes, dimethyl disulfide (198.0 mL, 0.200 mmol) was added. After stirring further for 1 hour, water was added to the reaction mixture, the organic solvents were removed by concentration under reduced-pressure, and the residue was extracted with diethyl ether. The organic layer was washed with brine, dried over anhydrous sodium sulfate, and concentrated under reduced pressure. The residue was recrystallized from diethyl ether-hexane to yield. 2-(4-methylthio-3,5-dimethoxyphenyl)-4,4-dimethyl-2-oxazoline as colorless fine needles (melting point: 82.5–84.5° C.) (34.80 g, yield: 0.76%).

A solution of 2-(4-methylthio-3,5-dimethoxyphenyl)-4,4-dimethyl-2-oxazoline (34.70 g, 0.123 mmol) in 3.0 M hydrochloric acid (450 mL) was stirred at 100° C. for 3 hours, and the reaction mixture was extracted with methanol-chloroform (1:10). The organic layer was washed with brine, dried over anhydrous sodium sulfate, and concentrated under reduced pressure. To a solution of the residue in methanol (50 mL) was added a 2.5 M aqueous sodium hydroxide (100 mL, 0.25 mol), and the resulting mixture u as stirred at 100° C. for 1 hour. The ice-cold reaction mixture was acidified by the addition of concentrated hydrochloric acid, and extracted with methanol-chloroform (1:10). The organic layer was washed with brine, dried over anhydrous sodium sulfate, and concentrated under reduced pressure to yield an oil (30.72 g) containing 3,5-dimethoxy-4-methylthiobenzoic acid.

Synthesis of the title compound from the oil obtained by the above-described procedure was carried out by applying the synthetic procedure of 4-benzyloxy-3,5-dimethoxyphenylboronic acid from the oil containing 4-benzyloxy-3,5-dimethoxybenzoic acid in Reference Example 8. From the oil (30.72 g) obtained by the above-described procedure, N-t-butoxycarbonyl-3,5-dimethoxy-4-methylthioaniline was obtained as colorless fine crystals (melting point: 123.5–125.5° C.) [26.33 g, yield: 71% based on 2-(4-methyl-thio-3,5-dimethoxyphenyl)-4,4-dimethyl-2-oxazoline]. From N-t-butoxycarbonyl-3,5-dimethoxy-4-methylthioaniline (12.74 g, 42.6 mmol), 1-iodo-3,5-dimethoxy-4-methylthiobenzene was obtained as a brown crystalline powder (melting point: 103.0–104.0° C.) (8.90 g, yield: 67%). From 1-iodo-3,5-dimethoxy-4-methylthiobenzene (6.90 g, 22.2 mmol), the title compound was obtained as a colorless crystalline powder (melting point: 262.0–265.0° C.) (4.11 g, yield: 82%).

REFERENCE EXAMPLE 10

4-Chloro-3,5-dimethoxyphenylboronic Acid

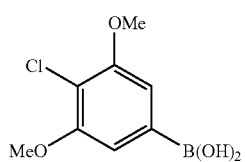

A solution of sodium nitrite (97.0 mg, 1.40 mmol) in water (2.0 mL) was added dropwise to an ice-cold suspension of 4-bromo-2,6-dimethoxyaniline (Z. Naturforsch., B24 (5), 524–527 (1969)) (232.0 mg, 1.00 mmol) in 6.0 M hydrochloric acid (2.5 mL). After stirring in ice for 30 minutes, a solution of cupric chloride (495.0 mg, 5.00 mmol) in concentrated hydrochloric acid (2.0 mL) was added. The reaction mixture was stirred at room temperature for 30 minutes and at 100° C. for 2 hours, and extracted with ethyl acetate. The organic layer was washed with a saturated aqueous sodium hydrogencarbonate and water, dried over anhydrous sodium sulfate, and concentrated under reduced pressure. The residue was purified by column chromatography on silica gel to yield 1-bromo-4-chloro-3,5-dimethoxybenzene as a colorless amorphous powder (230.0 mg, yield: 92%).

By a similar procedure to that described in Reference Example 2, crude crystals were obtained from 1-bromo-4-chloro-3,5-dimethoxybenzene (160.0 mg, 0.630 mmol). The crude crystals were purified by column chromatography on silica gel to yield the title compound as a colorless amorphous powder (90.0 mg, yield: 66%).

REFERENCE EXAMPLE 11

4-Cyano-3,5-dimethoxyphenylboronic Acid

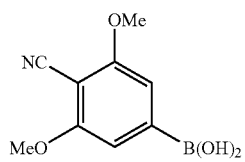

Following the procedure of the synthesis of 3,4,5-triethoxy-1-iodobenzene from the oil containing 3,4,5-triethoxyaniline in Reference Example 5,1-iodo-3,5-dimethoxy-4-methylbenzene was obtained as a pale yellow amorphous powder (7.59 g, yield: 87%) from 3,5-dimethoxy-4-methylaniline (J. Chem. Soc., 497–506 (1963)) (5.23 g, 31.3 mmol).

To a solution of 1-iodo-3,5-dimethoxy-4-methylbenzene (8.05 g, 28.9 mmol) in pyridine (83 mL) was added potassium permanganate (27.4 g, 173.4 mmol), and the resulting mixture was stirred at room temperature for 30 minutes and at 50° C. for 2 hours. Insoluble materials were removed by filtration through Celite, and the residue was washed with a 0.1 M aqueous sodium hydroxide. The filtrate and the washing were combined and washed with diethyl ether. The aqueous layer was acidified by the addition of concentrated hydrochloric acid, and extracted with chloroform. The organic layer was washed with brine, dried over anhydrous sodium sulfate, and concentrated under reduced pressure. The residue was suspended in hexane and filtered to yield 4-iodo-2,6-dimethoxybenzoic acid (5.57 g) as a pale brown crystalline powder (melting point: 197.5–204.0° C.) (5.57 g, yield: 63%).

Dimethylformamide (15 mg, 0.21 mmol) and oxalyl chloride (0.90 mL, 9.8 mmol) were added to an ice-cold solution of 4-iodo-2,6-dimethoxybenzoic acid (2.00 g, 6.50 mmol) in methylene chloride (10 mL). The mixture was stirred for 20 minutes, followed by the addition of concentrated aqueous ammonia (20 mL; 450 mmol). The reaction mixture was stirred at room temperature for 20 minutes and concentrated under reduced pressure to yield an oil (2.00 g) containing 4-carbamoyl-1-iodo-3,5-dimethoxybenzene.

To a solution of the oil (2.00 g) obtained by the above-described procedure in tetrahydrofuran (20 mL) were added carbon tetrachloride (10.0 mL, 104 mmol) and triphenylphosphine (3.50 g, 13.00 mmol), The reaction mixture was stirred at 50° C. for 20 hours, and concentrated under reduced pressure. The residue was purified by column chromatography on silica gel to yield 4-cyano-1-iodo-3,5-dimethoxybenzene as a colorless oil (1.55 g, yield: 82% based on 4-iodo-2,6-dimethoxybenzoic acid).

Following the procedure of Reference Example 2, the title compound was obtained as a colorless amorphous powder (360.0 mg, yield: 72%) from 4-cyano-1-iodo-3,5-dimethoxy-benzene (700.0 mg, 2.42 mmol).

REFERENCE EXAMPLE 12

4-(t-Butyldimethylsiloxy)methyl-3,5-dimethoxyphenyl trifluoromethanesulfonate

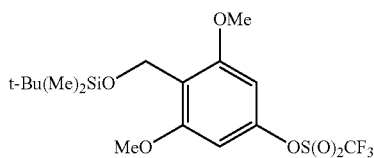

To a solution of 3,5-dimethoxyphenol (6.73 g, 43.7 mmol) in anhydrous dimethylformamide (50 mL) were added imidazole (5.95 g, 87.4 mmol) and t-butylchlorodiphenylsilane (15.0 g, 54.6 mmol), and the mixture was stirred at 50° C. for 4 hours. Water was added to the reaction mixture, and the mixture was extracted with ethyl acetate-hexane (1:2). The organic layer was washed with water, dried over anhydrous sodium sulfate, and then concentrated under reduced pressure. The residue was purified by column chromatography on silica gel to yield 1-t-butyldiphenylsiloxy-3,5-dimethoxybenzene as a colorless crystalline powder (melting point: 95.5–96.5° C.) (16.14 g, yield: 94%).

Under nitrogen, a 1.60 M solution of n-butyl lithium in hexane (31 mL, 49 mmol) was added to a solution of 1-t-butyldiphenylsiloxy-3,5-dimethoxybenzene (14.68 g, 39.0 mmol) in anhydrous diethyl ether (200 mL) stirred in an ice bath. The reaction mixture was stirred at 35° C. for 3 hours and cooled in the ice bath, followed by the addition of dimethylformamide (9.21 mL, 119.4 mmol). After stirring at room temperature for 1 hour, saturated aqueous ammonium chloride was added, and the mixture was extracted with diethyl ether. The organic layer was dried over anhydrous magnesium sulfate, and concentrated under reduced pressure. The residue was purified by column chromatography on silica gel to yield 4-t-butyldiphenylsiloxy-2,6-dimethoxybenzaldehyde as a colorless crystalline powder (melting point: 177.5–120.0° C.) (6.77 g, yield: 41%).

Sodium borohydride (519.0 mg, 13.73 mmol) was added to an ice-cold solution of 4-t-butyldiphenylsiloxy-2,6-dimethoxybeenzaldehyde (3.85 g, 9.15 mmol) in tetrahydrofuran (40 mL), and the mixture was stirred at room temperature for 2 hours and 30 minutes. Water was added to the reaction mixture, and the mixture was extracted with ethyl acetate. The organic layer was washed with brine, dried over anhydrous sodium sulfate, and concentrated under reduced pressure to afford crude 4-t-butyldiphenylsiloxy-2,6-dimethoxybenzyl alcohol as a colorless crystalline powder (melting point: 127.5–129.0° C.) (4.01 g).

To a solution of the crude 4-t-butyldiphenylsiloxy-2,6-dimethoxybenzyl alcohol (4.01 g) obtained by the above-described procedure in anhydrous dimethylformamide (30 mL) were added imidazole (1.29 g, 18.98 mmol) and t-butylchlorodimethylsilane (1.79 g, 11.86 mmol). After stirring at 50° C. for 4 hours, water was added and the resulting mixture was extracted with ethyl acetate-hexane (1:2). The organic layer was washed with water, dried over anhydrous sodium sulfate, and concentrated under reduced pressure to yield crude 4-(t-butyldimethylsiloxy)methyl-1-t-butyldiphenylsiloxy-3,5-dimethoxybenzene was obtained as a colorless amorphous powder (5.33 g).

To a solution of the crude 4-(t-butyldimethylsiloxy)methyl-1-t-butyldiphenylsiloxy-3,5-dimethoxybenzene (5.33 g) obtained by the above-described procedure in tetrahydrofuran (60 mL) was added a 1.0 M solution of tetrabutylammonium fluoride in tetrahydrofuran (9.9 mL, 9.9 mmol). After stirring at room temperature for 5 minutes, brine was added and the mixture was extracted with ethyl acetate. The organic layer was dried over magnesium sulfate and concentrated under reduced pressure. The residue was purified by column chromatography on silica gel to yield 4-(t-butyldimethylsiloxy)methyl-3,5-dimethoxyphenol as a colorless amorphous powder (1.93 g, yield: 75% based on. 4-t-butyldiphenylsiloxy-2,6-dimethoxybenzaldehyde).

Following the procedure of Reference Example 3, the title compound was obtained as a colorless amorphous powder from 4-(t-butyldimethylsiloxy)methyl-3,5-dimethoxyphenol (1.93 g, 6.79 mmol)(1.57 g, yield: 54%).

REFERENCE EXAMPLE 13

4-Ethoxycarbonyl-1-iodo-3,5-dimethoxybenzene

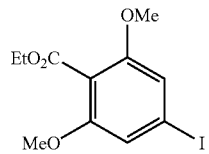

To a solution of 4-iodo-2,6-dimethoxybenzoic acid (603.0 mg, 1.96 mmol), synthesized by the process described in Reference Example 11, in methylene chloride (12 mL) were added dimethylformamide (0.020 mL, 0.26 mmol) and oxalyl chloride (0.26 mL, 3.0 mmol). After stirring at room temperature for 30 minutes, the resulting solution was poured into an ice-cold solution of triethylamine (0.50 mL, 3.6 mmol) in ethanol (10 mL). The reaction mixture was stirred at room temperature for 30 minutes and concentrated under reduced pressure. A solution of the residue in diethyl ether was washed successively with water, 0.1 M hydrochloric acid and brine, dried over anhydrous sodium sulfate, and concentrated under reduced pressure. The residue was purified by column chromatography on silica gel to yield the title compound as a colorless oil (641.0 mg, yield: 97%).

REFERENCE EXAMPLE 14

4-t-Butoxycarbonyl-3,5-dimethoxyphenylboronic Acid

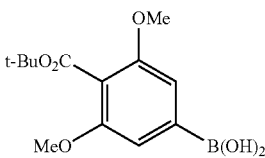

Following the procedure described in Reference Example 13, crude 4-t-butoxycarbonyl-1-iodo-3,5-dimethoxybenzene was obtained as a colorless amorphous powder (2.33 g) from 4-iodo-2,6-dimethoxybenzoic acid (2.40 g, 7.79 mmol).

Following the procedure of Reference Example 2, an oil was obtained from the crude 4-t-butoxycarbonyl-1-iodo-3,5-dimethoxybenzene (1.99 g, approx. 5.48 mmol) obtained by the above-described procedure. Diethyl ether-hexane was added to the oil and the resulting precipitate was collected by filtration to yield the title compound as a colorless crystalline powder (melting point: ≧300.0° C.) (1.06 g, yield: 56% based on 4-iodo-2,6-dimethoxybenzoic acid).

REFERENCE EXAMPLE 15

4-Acetyl-3,5-dimethoxyphenyl trifluoromethanesulfonate

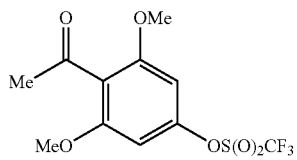

Under nitrogen, a solution of the 1-t-butyldiphenylsiloxy-3,5-dimethoxybenene (7.85 g, 22.0 mmol), which had been synthesized by the process described in Reference Example. 12, in anhydrous diethyl ether (80 mL) was stirred in an ice bath, and a 1.59 M solution of n-butyl lithium in hexane (16.6 mL, 26.6 mmol) was added. After the reaction mixture was stirred at 35° C. for 1 hour and 30 minutes, it was again stirred in the ice bath, then acetyl chloride (2.34 mL, 33.0 mmol) was added. After stirring at room temperature for 30 minutes, saturated aqueous ammonium chloride was added, and the mixture was extracted with diethyl ether. The organic layer was washed with water, dried over anhydrous magnesium sulfate, and concentrated under reduced pressure. The residue was purified by column chromatography on silica gel to yield 4-t-butyldiphenylsiloxy-2,6-dimethoxyacetophenone as a colorless oil (2.07 g, yield: 22%).

To a solution of 4-t-butyldiphenylsiloxy-2,6-dimethoxyacetophenone (2.07 g, 4.76 mmol) in tetrahydrofuran (42 mL) was added a 1.0 M solution of tetrabutylammonium fluoride in tetrahydrofuran (5.2 mL, 5.2 mmol). The reaction mixture was stirred at room temperature for 5 minutes and concentrated under reduced pressure. A solution of the residue in methylene chloride (63 mL) was stirred in a dry ice-methanol bath. After the addition of N,N-diisopropylethylamine (2.1 mL, 12 mmol), trifluoromethanesulfonic anhydride (1.2 mL, 7.1 mmol) was added dropwise. The reaction mixture was stirred for 30 minutes in the dry ice-methanol bath, washed with 1.0 M hydrochloric acid and brine, dried over anhydrous sodium sulfate, and concentrated under reduced pressure. The residue was purified by column chromatography on silica gel to yield the title compound as a colorless oil (11.21 g, yield: 78%).

EXAMPLE 1

1,4-Bis(5-phenyl-2-pyridyl)hexahydro-1,4-diazepine

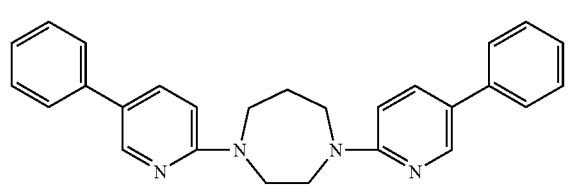

Under nitrogen, to a solution of the 1,4-bis(5-bromo-2-pyridyl)hexahydro-1,4-diazepine (200 mg, 0.585 mmol) synthesized in Reference Example 1 in ethanol-toluene (2.0 mL-2.0 mL) were added phenylboronic acid (130.0 mg, 1.07 mmol), tetrakis(triphenylphosphine)palladium (56.0 mg, 0.050 mmol) and a 2.0 M aqueous potassium carbonate (0.5 mL, 1.0 mmol), and the resulting mixture was stirred at 80° C. for 3 hours. After cooling, the organic layer was collected and the aqueous layer was extracted with chloroform. The organic layers were combined, dried over anhydrous sodium sulfate, and concentrated under reduced pressure. The residue was purified by column chromatography on silica gel to yield crude crystals. The crude crystals were recrystallized from chloroform-hexane to yield the title compound as slightly yellow needles (melting point: 221.0–222.0° C.) (61.0 mg, yield: 31%).

$^1$H-NMR (CDCl$_3$) δ: 2.17 (tt, J=6.3, 6.3 Hz, 2H), 3.65 (dd, J=6.3, 6.3 Hz, 4H), 3.96 (s, 4H), 6.64 (d, J=8.8 Hz, 2H), 7.30 (t, J=7.3 Hz, 2H), 7.42 (t, J=7.3 Hz; 4H), 7.52 (d, J=7.3 Hz, 4H), 7.70 (dd, J=2.4, 8.8 Hz, 2H), 8.43(d, J=2.4 Hz, 2H).

EXAMPLE 2

1,4-Bis[5-(2-methoxyphenyl)-2-pyridyl]hexahydro-1,4-diazepine

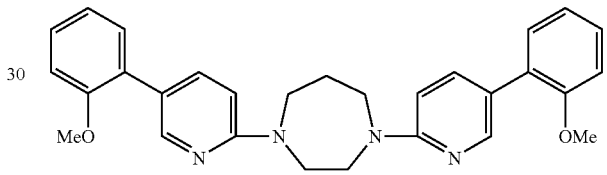

Following the procedure of Example 1, crude crystals were obtained from 1,4-bis(5-bromo-2-pyridyl)hexahydro-1,4-diazepine (206.0 mg, 0.500 mmol) synthesized in Reference Example 1 and 2-methoxyphenylboronic acid (182.0 mg, 1.20 mmol). The crude crystals were recrystallized from methylene chloride-hexane to yield the title compound as slightly yellow needles (melting point: 161.0–162.0° C.) (215.0 mg, yield: 92%).

$^1$H-NMR (CDCl$_3$) δ: 2.16 (tt, J=6.0, 6.0 Hz, 2H), 3.64 (dd, J=6.0, 6.0 Hz, 4H), 3.83 (s, 6H), 3.95 (s, 4H), 6.60 (d, J=8.7 Hz, 2H), 6.65–7.06 (m, 4H), 7.28–7.33 (m, 4H), 7.69 (dd, J=2.4, 8.7 Hz, 2H), 8.36 (d, J=2.4 Hz, 2H).

EXAMPLE 3

1,4-Bis[5-(3-methoxyphenyl)-2-pyridyl]hexahydro-1,4-diazepine

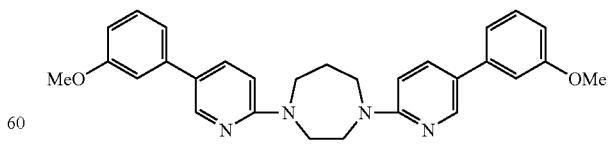

Following the procedure of Example 1, crude crystals were obtained from 1,4-bis(5-bromo-2-pyridyl)hexahydro-1,4-diazepine (206.0 mg, 0.500 mmol)-synthesized in Reference Example 1 and 3-methoxyphenylboronic acid (182.0 mg, 1.20 mmol). The crude crystals were recrystallized from methylene chloride-hexane to yield the title compound as slightly yellow flakes (melting point: 146.0–149.0° C.) (121.0 mg, yield: 52%).

$^1$H-NMR (CDCl$_3$) δ: 2.16 (tt, J=6.0, 6.0 Hz, 2H), 3.63 (dd, J=6.0, 6.0 Hz, 4H), 3.85 (s, 6H), 3.95 (s, 4H), 6.62 (d, J=8.7 Hz, 2H), 6.84 (ddd, J=1.9, 2.4, 8.0 Hz, 2H), 7.05 (dd, J=1.9, 2.4 Hz, 2H), 7.15 (ddd, J=2.4, 2.4, 7.8 Hz, 2H), 7.33 (dd, J=7.8, 8.0 Hz, 2H), 7.68 (dd, J=2.4, 8.7 Hz, 2H), 8.42 (d, J=2.4 Hz, 2H).

EXAMPLE 4

1,4-Bis[5-(4-methoxyphenyl)-2-pyridyl]hexahydro-1,4-diazepine

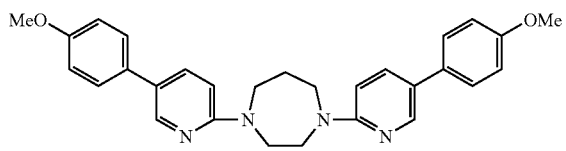

Following the procedure of Example 1, crude crystals were obtained from 1,4-bis(5-bromo-2-pyridyl)hexahydro-1,4-diazepine (206.0 mg, 0.500 mmol) synthesized in Reference Example 1 and 4-methoxyphenylboronic acid (182.0 mg, 1.20 mmol). The crude crystals were recrystallized from chloroform-hexane to yield the title compound as pale yellow needles (melting point: 254.0–256.0° C.) (98.0 mg, yield: 42%).

$^1$H-NMR (CDCl$_3$) δ: 2.16 (tt, J=6.0, 6.0 Hz, 2H), 3.62 (dd, J=6.0, 6.0 Hz, 4H), 3.84 (s, 6H), 3.94 (s, 4H), 6.61 (d, J=8.7 Hz, 2H), 6.96 (d, J=8.7 Hz, 4H), 7.43 (d, J=8.7 Hz, 4H), 7.64 (dd, J=2.4, 8.7 Hz, 2H), 8.37 (d, J=2.4 Hz, 2H).

EXAMPLE 5

1,4-Bis[5-(4-methylthiophenyl)-2-pyridyl]hexahydro-1,4-diazepine

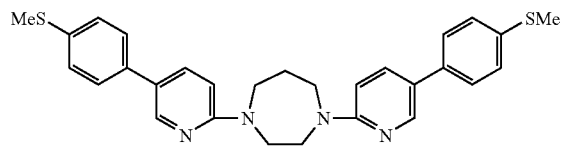

Following the procedure of Example 1, crude crystals were obtained from the 1,4-bis(5-bromo-2-pyridyl)hexahydro-1,4-diazepine (206.0 mg, 0.500 mmol) synthesized in Reference Example 1 and 4-methylthiophenylboronic acid (202.0 mg, 1.20 mmol). The crude crystals were recrystallized from chloroform-hexane to yield the title compound as pale yellow needles (melting point: 252.0–255.0° C.) (109.0 mg, yield: 43%).

$^1$H-NMR (CDCl$_3$) δ: 2.16 (tt, J=6.0, 6.0 Hz, 2H), 2.51 (s, 6H), 3.63 (dd, J=6.0, 6.0 Hz, 4H), 3.94 (s, 4H), 6.61 (d, J=8.7 Hz, 2H), 7.31 (d, J=8.2 Hz, 4H), 7.43 (d, J=8.2 Hz, 4H), 7.66 (dd, J=2.4, 8.7 Hz, 2H), 8.40 (d, J=2.4 Hz, 2H).

EXAMPLE 6

1,4-Bis[5-(4-methylphenyl)-2-pyridyl]hexahydro-1,4-diazepine

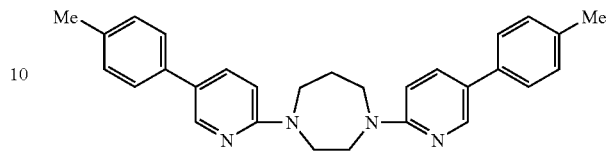

Following the procedure of Example 1, crude crystals were obtained from the 1,4-bis(5-bromo-2-pyridyl)hexahydro-1,4-diazepine (206.0 mg, 0.500 mmol) synthesized in Reference Example 1 and 4-methylphenylboronic acid (163.0 mg, 1.20 mmol). The crude crystals were recrystallized from chloroform-hexane to yield the title compound as pale yellow needles (melting point: 245.0–247.0° C.)(93.0 mg, yield: 42%).

$^1$H-NMR (CDCl$_3$) δ: 2.16 (tt, J=6.0, 6.0 Hz, 2H), 2.38 (s, 6H), 3.63 (dd, J=6.0, 6.0 Hz, 4H), 3.94 (s, 4H), 6.62 (d, J=8.7 Hz, 2H), 7.22 (d, J=8.0 Hz, 4H), 7.41 (d, J=8.0 Hz, 4H), 7.67 (dd, J=2.4, 8.7 Hz, 2H), 8.40 (d, J=2.4 Hz, 2H).

EXAMPLE 7

1,4-Bis[5-(4-t-butylphenyl)-2-pyridyl]hexahydro-1,4-diazepine

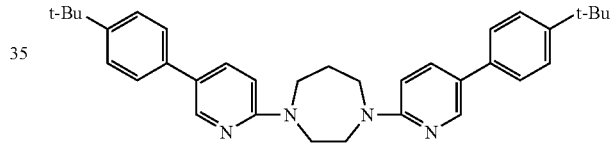

Following the procedure of Example 1, crude crystals were obtained from the 1,4-bis(5-bromo-2-pyridyl)hexahydro-1,4-diazepine (206.0 mg, 0.500 mmol) synthesized in Reference Example 1 and 4-t-butylphenylboronic acid: (226.0 mg, 1.20 mmol). The crude crystals were recrystallized from chloroform-hexane to yield the title compound as colorless needles (melting point: 268.0–270.0° C.) (117.0 mg, yield: 42%).

$^1$H-NMR (CDCl$_3$) δ: 1.35 (s, 18H), 2.17 (tt, J=6.0, 6.0 Hz, 2H), 3.64 (dd, J=6.0, 6.0 Hz, 4H), 3.96 (s, 4H), 6.63 (d, J=8.7 Hz, 2H), 7.45 (s, 8H), 7.67 (dd, J=2.4, 8.7 Hz, 2H), 8.42 (d, J=2.4 Hz, 2H).

EXAMPLE 8

1,4-Bis[5-(4-trifluoromethylphenyl)-2-pyridyl]hexahydro-1,4-diazepine

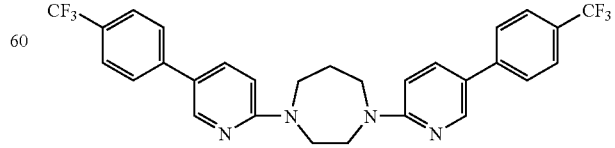

Following the procedure of Example 1, crude crystals were obtained from the 1,4-bis(5-bromo-2-pyridyl)hexahydro-1,4-diazepine (206.0 mg, 0.500 mmol) synthesized in Reference Example 1 and 4-trifluoromethylphenylboronic acid (227.0 mg, 1.20 mmol). The crude crystals were recrystallized from chloroform-hexane to yield the title compound as colorless needles (melting point: 236.0–238.0° C.) (110.0 mg, yield: 40%).

$^1$H-NMR (CDCl$_3$) δ: 2.16 (tt, J=6.0, 6.0 Hz, 2H), 3.66 (dd, J=6.0, 6.0 Hz, 4H), 3.97 (s, 4H), 6.65 (d, J=8.7 Hz, 2H), 7.60 (d, J=8.5 Hz, 4H), 7.66 (d, J=8.5 Hz, 4H), 7.70 (dd, J=2.4, 8.7 Hz, 2H), 8.43 (d, J=2.4 Hz, 2H).

EXAMPLE 9

1,4-Bis[5-(4-fluorophenyl)-2-pyridyl]hexahydro-1,4-diazepine

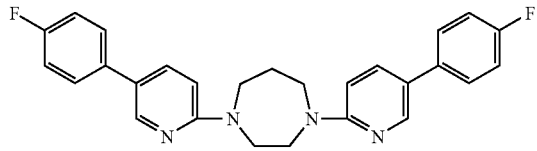

Following the procedure of Example 1, crude crystals were obtained from 1,4-bis(5-bromo-2-pyridyl)hexahydro-4-diazepine (206.0 mg, 0.500 mmol) synthesized in Reference Example 1 and 4-fluorophenylboronic acid (168.0 mg, 1.20 mmol). The crude crystals were recrystallized from chloroform-hexane to yield the title compound as colorless needles (melting point: 268.0–270.0° C.) (115.0 mg, yield: 52%).

$^1$H-NMR (CDCl$_3$) δ: 2.16 (tt, J=6.0, 6.0 Hz, 2H), 3.64 (dd, J=6.0, 6.0 Hz, 4H), 3.95 (s, 4H), 6.62 (d, J=8.7 Hz, 2H), 7.10 (dd, J=8.7 Hz, $^3J_{HF}$=8.7 Hz, 4H), 7.45 (dd, J=8.7 Hz, $^4J_{HF}$=5.3 Hz, 4H), 7.63 (d, J=2.4, 8.7 Hz, 2H), 8.36 (d, J=2.4 Hz, 2H).

EXAMPLE 10

1,4-Bis[5-(4-chlorophenyl)-2-pyridyl]hexahydro-1,4-diazepine

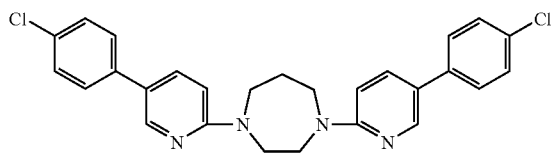

Following the procedure of Example 1, crude crystals were obtained from 1,4-bis(5-bromo-2-pyridyl)hexahydro-1,4-diazepine (206.0 mg, 0.500 mmol) and 4-chlorophenylboronic acid (188.0 mg, 1.20 mmol). The crude crystals were recrystallized from chloroform-hexane to yield the title compound as colorless needles (melting point: 245.0–247.0° C.) (105.0 mg, yield: 44%).

$^1$H-NMR (CDCl$_3$) δ: 2.15 (tt, J=6.0, 6.0 Hz; 2H), 3.63 (dd, J=6.0, 6.0 Hz, 4H), 3.95 (s, 4H), 6.62 (d, J=8.7 Hz, 2H), 7.37 (d, J=8.2 Hz, 4H), 7.43 (d, J=8.2 Hz, 4H), 7.64 (dd, J=2.4, 8.7 Hz, 2H), 8.38 (d, J=2.4 Hz, 2H).

EXAMPLE 11

1,4-Bis[5-(2,3-dimethoxyphenyl)-2-pyridyl]hexahydro-1,4-diazepine dimethanesulfonate

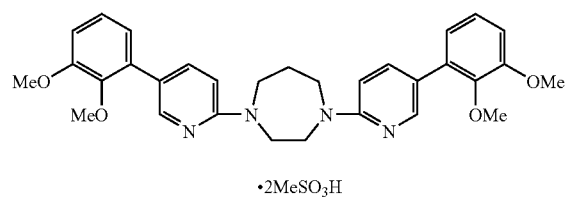

Following the procedure of Example 1, 1,4-bis[5-(2,3-dimethoxyphenyl)-2-pyridyl]hexahydro-1,4-diazepine was obtained as a colorless oil (28.0 mg, yield: 26%) from 1,4-bis(5-bromo-2-pyridyl)hexahydro-1,4-diazepine (82.0 mg, 0.200 mmol) synthesized in Reference Example 1 and 2,3-dimethoxyphenylboronic acid (*Bull. Soc. Chim. Fr.*, 767–769 (1973)) (146.0 mg, 0.800 mmol) synthesized in a similar manner to that described in Reference Example 2.

To a solution of 1,4-bis[5-(2,3-dimethoxyphenyl)-2-pyridyl]hexahydro-1,4-diazepine (28.0 mg, 0.053 mmol) in chloroform (3.0 mL) was added a 1.0 M solution of methane-sulfonic acid in methanol (0.11 mL, 0.11 mmol), and the reaction mixture was concentrated under reduced pressure. The residue was recrystallized from methylene chloride-methanol-diethyl ether to yield the title compound as a pale brown crystalline powder (melting point: 199.5–202.0° C.) (32.3 mg, yield: 86%).

$^1$H-NMR (CDCl$_3$) (ammonium salt NH$^+$ protons were not observed) δ: 1.85–2.43 (m, 2H), 2.90 (s, 6H), 3.69 (s, 6H), 3.90 (s, 6H), 3.95–4.10 (m, 4H), 4.31 (s, 4H), 6.88 (br.d, J=6.0 Hz, 2H), 6.97 (br.d, J=6.0 Hz, 2H), 7.11 (br.dd, J=6.0 Hz, 6.0 Hz, 2H), 7.26 (br.d, J=7.6 Hz, 2H), 8.20 (br.d, J=7.6 Hz, 2H), 8.35 (br.s, 2H).

EXAMPLE 12

1,4-Bis[5-(2,4-dimethoxyphenyl)-2-pyridyl]hexahydro-1,4-diazepine

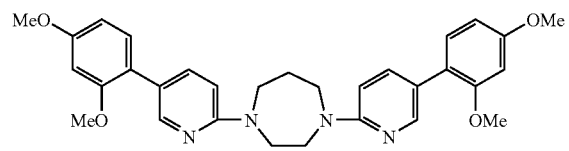

Following the procedure of Example 1, crude crystals were obtained from 1,4-bis(5-bromo-2-pyridyl)hexahydro-1,4-diazepine (206.0 mg, 0.500 mmol) synthesized in Reference Example 1 and 2,4-dimethoxyphenylboronic acid (218.0 mg, 1.20 mmol). The crude crystals were recrystallized from chloroform-hexane to yield the title compound as colorless needles (melting point: 161.0–163.0° C.)(206.0 mg, yield: 78%).

$^1$H-NMR (CDCl$_3$) δ: 2.15 (tt, J=6.0, 6.0 Hz, 2H), 3.63 (dd, J=6.0, 6.0 Hz, 4H), 3.80 (s, 6H), 3.84 (s, 6H), 3.93 (s, 4H), 6.54–6.57 (m, 4H), 6.58 (d, J=8.7 Hz, 2H), 7.21 (d, J=9.0 Hz, 2H), 7.64 (dd, J=2.4, 8.7 Hz, 2H), 8.30 (d, J=2.4 Hz, 2H).

EXAMPLE 13

1,4-Bis[5-(2,6-dimethoxyphenyl)-2pyridyl]hexahydro-1,4-diazepine

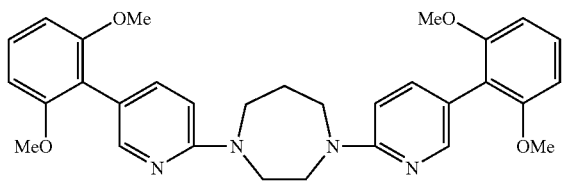

Following the procedure of Example 1, an oil was obtained from 1,4-bis(5-bromo-2-pyridyl)hexahydro-1,4-diazepine (100.0 mg, 0.240 mmol) synthesized in Reference Example 1 and 2,6-dimethoxyphenylboronic acid (*Chem. Abs.*, 123, pr256679r.) (150.0 mg, 1.00 mmol). Methanol-chloroform-hexane was added to the oil, and the resulting precipitate was collected by filtration to yield the title compound as a pale yellow crystalline powder (melting point: ≧300.0° C.) (24.0 mg, yield: 19%).

$^1$H-NMR [CD$_3$OD-CDCl$_3$(1:10)]δ: 2.16 (tt, J=6.1, 6.1 Hz, 2H), 3.67 (dd, J=6.1, 6.1 Hz, 4H), 3.77 (s, 12H), 3.92 (s, 4H), 6.64 (d, J=8.7 Hz, 2H), 6.66 (d, J=8.5 Hz, 4H), 7.26 (t, J=8.5 Hz, 2H), 7.54 (dd, J=2.2, 8.7 Hz, 2H), 8.15 (d, J=2.2 Hz, 2H).

EXAMPLE 14

1,4-Bis[5-(3,4-dimethoxyphenyl)-2-pyridyl]hexahydro-1,4-diazepine

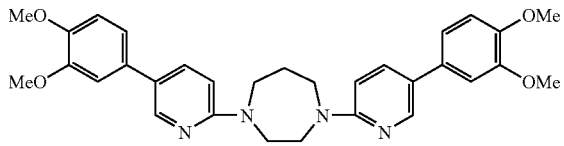

Following the procedure of Example 1, crude crystals were obtained from 1,4-bis(5-bromo-2-pyridyl)hexahydro-1,4-diazepine (206.0 mg, 0.500 mmol) synthesized in Reference Example 1 and 3,4-dimethoxyphenylboronic acid (218.0 mg, 1.20 mmol). The crude crystals were recrystallized from chloroform-hexane to yield the title compound as pale yellow needles (melting point: 190.0–192.0° C.) (129.0 mg, yield: 48%).

$^1$H-NMR (CDCl$_3$) δ: 2.16 (tt, J=6.0, 6.0 Hz, 2H), 3.63 (dd, J=6.0, 6.0 Hz, 4H), 3.91 (s, 6H), 3.93 (s, 6H), 3.95 (s, 4H), 6.62 (d, J=8.7 Hz, 2H), 6.93 (d, J=8.2 Hz, 2H), 7.02 (d, J=1.9 Hz, 2H), 7.05 (dd, J=1.9, 8.2 Hz, 2H), 7.65 (dd, J=2.4, 8.7 Hz, 2H), 8.39 (d, J=2.4 Hz, 2H).

EXAMPLE 15

1,4-Bis[5-(3,4-methylenedioxyphenyl)-2-pyridyl]hexahydro-1,4-diazepine

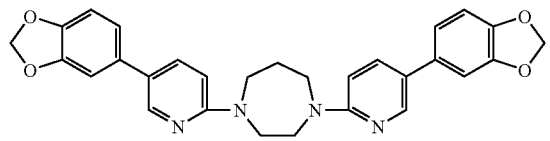

Following the procedure of Example 1, crude crystals were obtained from 1,4-bis(5-bromo-2-pyridyl)hexahydro-1,4-diazepine (206.0 mg, 0.500 mmol) synthesized in Reference Example 1 and 3,4-methylenedioxyphenylboronic acid (199.0 mg, 1.20 mmol). The crude crystals were recrystallized from chloroform-hexane to yield the title compound as pale yellow needles (melting point: 235.0–237.0° C.) (105.0 mg, yield: 42%).

$^1$H-NMR (CDCl$_3$) δ: 2.15 (tt, J=6.0, 6.0 Hz, 2H), 3.62 (dd, J=6.0, 6.0 Hz, 4H), 3.93 (s, 4H), 5.98 (s, 4H), 6.59 (d, J=8.7 Hz, 2H), 6.86 (d, J=8.0 Hz, 2H), 6.95 (dd, J=1.7, 8.0 Hz, 2H), 6.98 (d, J=1.7 Hz, 2H), 7.60 (dd, J=2.4, 8.7 Hz, 2H), 8.32 (d, J=2.4 Hz, 2H).

EXAMPLE 16

1,4-Bis[5-(3,5-dimethoxyphenyl)-2-pyridyl]hexahydro-1,4-diazepine dimethanesulfonate

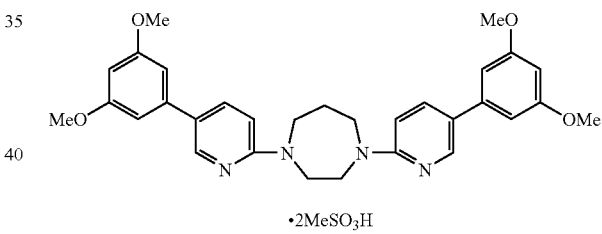

·2MeSO$_3$H

Following the procedure of Example 1, 1,4-bis[5-(3,5-dimethoxyphenyl)-2-pyridyl]hexahydro-1,4-diazepine was obtained as a colorless oil (89.0 mg, yield: 71%) from 1,4-bis(5-bromo-2-pyridyl)hexahydro-1,4-diazepine (100.0 mg, 0.240 mmol) synthesized in Reference Example 1 and 3,5-dimethoxyphenylboronic acid (79.0 mg, 0.530 mmol) synthesized in a similar manner to that described in Reference Example 2.

To a solution of 1,4-bis[5-(3,5-dimethoxyphenyl)-2-pyridyl]hexahydro-1,4-diazepine (89.0 mg, 0.170 mmol) in methanol (5.0 mL) was added a 1.0 M aqueous methanesulfonic acid (0.34 mL, 0.34 mmol), and the reaction mixture was concentrated under reduced pressure. Ethanol (5.0 mL) was added to the residue, and the resulting mixture was concentrated under reduced pressure. The residue was recrystallized from methanol-diethyl ether to yield the title compound as a pale yellow crystalline powder (melting point: 181.0–183.0° C.) (81.0 mg, yield: 66%).

$^1$H-NMR (CDCl$_3$) (ammonium salt NH$^+$ protons were not observed) δ: 2.35–2.45 (m, 2H), 2.91 (s, 6H), 3.81 (s, 12H), 3.95–4.10 (m, 4H), 4.31 (s, 4H), 6.47 (t, J=2.2 Hz, 2H), 6.55 (d, J=2.2 Hz, 4H), 7.34 (d, J=9.6 Hz, 2H), 8.12 (dd, J=2.2, 9.6. Hz, 2H), 8.36 (d, J=2.2 Hz, 2H).

EXAMPLE 17

1,4-Bis[5-(3,5-diethoxyphenyl)-2-pyridyl]hexahydro-1,4-diazepine

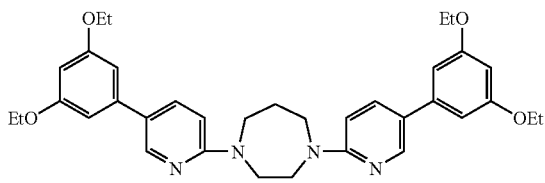

Under nitrogen, to a solution of 3,5-diethoxyphenyl trifluoromethanesulfonate (WO99/41224) (251.0 mg, 0.800 mmol) in dimethylformamide (6.5 mL) were added bis(pinacolato)diboron (223.0 mg, 0.880 mmol), dichloro[1,1'-bis(diphenyl-phosphino)ferrocene]palladium(II) dichloromethane complex (1:1) (19.6 mg, 0.024 mmol), 1,1'-bis(diphenylphosphino)ferrocene (13.3 mg, 0.024 mmol) and potassium acetate (236.0 mg, 2.40 mmol), and the resulting mixture was stirred at 80° C. for 12 hours. To the reaction mixture were added 1,4-bis(5-bromo-2-pyridyl)hexahydro-1,4-diazepine (110.0 mg, 0.270 mmol) synthesized by the process described in Reference Example 1, dichloro[1,1'-bis(diphenylphosphino)ferrocene]palladium(I) dichloromethane complex (1.1) (19.6 mg, 0.024 mmol) and a 2.0 M sodium carbonate (2.0 mL, 4.0 mmol). The resulting mixture was stirred at 80° C. for 1 hour. Water was added to the reaction mixture, and the mixture was extracted with diethyl ether. The organic layer was dried over anhydrous sodium sulfate and concentrated under reduced pressure. The residue was purified by column chromatography on silica gel to yield the title compound as a colorless amorphous powder (70.0 mg, yield: 45%).

$^1$H-NMR (CDCl$_3$) δ: 1.43 (t, J=7.0 Hz, 12H), 2.16 (tt, J=6.2, 6.2 Hz, 2H), 3.63 (dd, J=6.2, 6.2 Hz, 4H), 3.94 (s, 4H), 4.06 (q, J=7.0 Hz, 8H), 6.40 (t, J=2.2 Hz, 2H), 6.60 (d, J=8.9 Hz, 2H), 6.64 (d, J=2.2 Hz, 4H), 7.66 (dd, J=2.6, 8.9 Hz, 2H), 8.41 (d, J=2.6 Hz, 2H).

EXAMPLE 18

1,4-Bis[5-(3,5-diisopropoxyphenyl)-2-pyridyl]hexahydro-1,4-diazepine

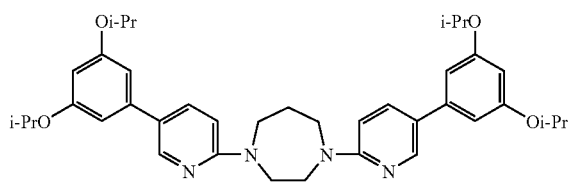

Following the procedure of Example 17, an oil was obtained from 1,4-bis(5-bromo-2-pyridyl)hexahydro-1,4-diazepine (103.0 mg, 0.250 mmol) synthesized in Reference Example 1 and 3,5-diisopropoxyphenyl trifluoromethanesulfonate (261.0 mg, 0.760 mmol) synthesized in Reference Example 3. Hexane was added to the oil, and the resulting precipitate was collected by filtration to yield the title compound as a colorless crystalline powder (melting point: 131.0–132.0° C.) (78.0 mg, yield: 49%).

$^1$H-NMR (CDCl$_3$) δ:1.36 (d, J=6.0 Hz, 24H), 2.16 (tt, J=6.2, 6.2 Hz, 2H), 3.63 (dd, J=6.2, 6.2 Hz, 4H), 3.94 (s, 4H), 4.57 (qq, J=6.0, 6.0 Hz, 4H), 6.39 (t, J=2.3 Hz, 2H), 6.60 (d, J=8.9 Hz, 2H), 6.62 (d, J=2.3 Hz, 4H), 7.66 (dd, J=2.6, 8.9 Hz, 2H), 8.40 (d, J=2.6 Hz, 2H).

EXAMPLE 19

1,4-Bis[5-(3,5-dimethylphenyl)-2-pyridyl]hexahydro-1,4-diazepine dimethanesulfonate

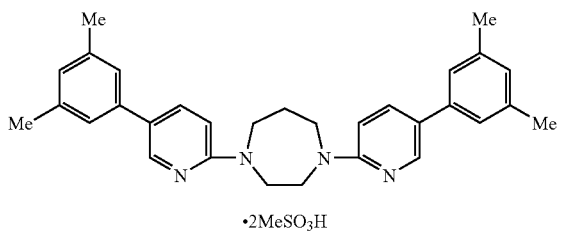

Following the procedure of Example 1, 1,4-bis[5-(3,5-dimethylphenyl)-2-pyridyl]hexahydro-1,4-diazepine was obtained as a yellow crystalline powder (83.0 mg, yield: 89%) from 1,4-bis(5-bromo-2-pyridyl)hexahydro-1,4-diazepine (82.0 mg, 0.200 mmol) synthesized in Reference Example 1 and 3,5-dimethylphenylboronic acid (90.0 mg, 0.600 mmol).

To a solution of 1,4-bis[5-(3,5-dimethylphenyl)-2-pyridyl]hexahydro-1,4-diazepine (83.0 mg, 0.170 mmol) in methanol (5.0 mL) was added a 1.0 M aqueous methanesulfonic acid (0.37 mL, 0.37 mmol), and the mixture was concentrated under reduced pressure. Ethanol (5.0 mL) was added to the residue, and the resulting mixture was concentrated under reduced pressure. The residue was recrystallized from ethanol-diethyl ether-hexane to yield the title compound as colorless needles [melting point: 188.0° C. (decomposed)](101.0 mg, yield: 86%).

$^1$H-NMR (DMSO-d$_6$, 120° C.)(ammonium salt NH$^+$ protons were not observed) δ: 2.02 (tt, J=5.8, 5.8 Hz, 2H), 2.28 (s, 12H), 2.46 (s, 6H), 3.78 (dd, J=5.8, 5.8 Hz, 4H), 4.01 (s, 4H), 6.94 (br.s, 2H), 6.99 (d, J=9.2 Hz, 2H), 7.09 (br.s, 4H), 7.88 (dd, J=2.4, 9.2 Hz, 2H), 8.19 (d, J=2.4 Hz, 2H).

EXAMPLE 20

1,4-Bis[5-[3,5-bis(methoxycarbonyl)phenyl]-2-pyridyl]hexahydro-1,4-diazepine

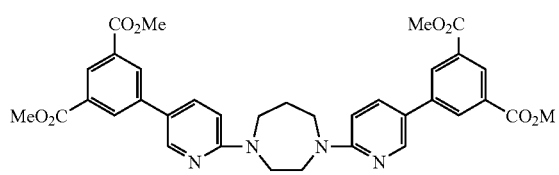

Following the procedure of Example 17, an oil was obtained from 1,4-bis(5-bromo-2-pyridyl)hexahydro-1,4-diazepine (207.8 mg, 0.504 mmol) synthesized in Reference Example 1 and 3,5-bis(methoxycarbonyl)phenyl trifluoromethanesulfonate (J. Org. Chem., 65, 5360–5370 (2000)) (474.4 mg, 1.39 mmol). Diethyl ether was added to the oil, and the resulting precipitate was collected by filtration to yield the title compound as a colorless crystalline powder (melting point: 216.0–217.5° C.) (92.8 mg, yield: 10%).

$^1$H-NMR (CDCl$_3$) δ: 2.17 (tt, J=6.1, 6.1 Hz, 2H), 3.66 (dd, J=6.1, 6.1 Hz, 4H), 3.97 (s, 12H), 3.98 (s, 4H), 6.66 (d, J=8.9 Hz, 2H), 7.76 (dd, J=2.5, 8.9 Hz, 2H), 8.38 (d, J=1.1 Hz, 4H), 8.49 (d, J=2.5 Hz, 2H), 8.58 (t, J=1.1 Hz, 2H).

EXAMPLE 21

1,4-Bis[5-[3,5-bis(hydroxymethyl)phenyl]-2-pyridyl]hexahydro-1,4-diazepine

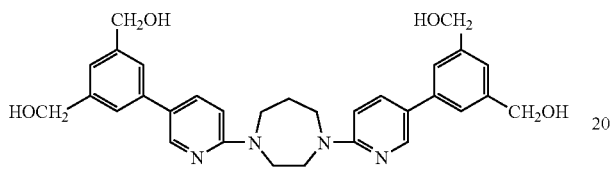

Under nitrogen, a solution of 1,4-bis[5-[3,5-bis(methoxycarbonyl)phenyl]-2-pyridyl]hexahydro-1,4-diazepine (17.0 mg, 0.0266 mmol), which had been synthesized in Example 20, in anhydrous tetrahydrofuran (1.0 mL) was cooled to −20° C. To the resulting solution was added a 1.0 M solution of diisobutylaluminum hydride in toluene (0.40 mL, 0.40 mmol), and the resulting mixture was stirred for 1 hour. Methanol (0.2 mL, 4.9 mmol) was added to the mixture, and the bath was removed, then 0.50 M hydrochloric acid (1.0 mL, 0.50 mmol) was added. The mixture was stirred at room temperature for 1 hour, and a 1.0 M aqueous sodium hydroxide (1.0 mL, 1.0 mmol) and brine were added. The resulting mixture was extracted with chloroform, and the organic layer was dried over anhydrous sodium sulfate and concentrated under reduced pressure. The residue was purified by preparative thin-layer chromatography on silica gel to yield the title compound as a colorless amorphous powder (7.4 mg, yield: 53%).

$^1$H-NMR (CD$_3$OD) δ: 2.31 (tt, J=5.9, 5.9 Hz, 2H), 3.86 (dd, J=5.9, 5.9 Hz, 4H), 4.14 (s, 4H), 4.83 (s, 8H), 6.98 (d, J=8.9 Hz, 2H), 7.46 (br.s, 2H), 7.60 (br.s, 4H), 7.97 (dd, J=2.3, 8.9 Hz, 2H), 8.51 (d, J=2.3 Hz, 2H).

EXAMPLE 22

1,4-Bis[5-[3,5 bis(methoxymethyl)phenyl]-2-Pyridyl]hexahydro-1,4-diazepine dihydrochloride

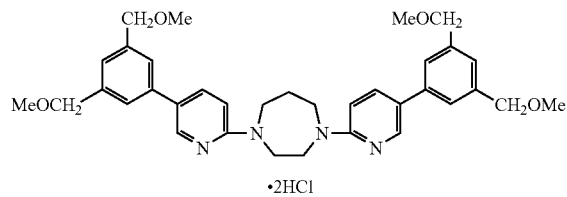

Following the procedure of Example 17, 1,4-bis[5-[3,5-bis(methoxymethyl)-phenyl]-2-pyridyl]hexahydro-1,4-diazepine was obtained as a colorless oil (51.9 mg, yield: 33%) from 1,4-bis(5-bromo-2-pyridyl)hexahydro-1,4-diazepine (99.5 mg, 0.242 mmol) synthesized in Reference Example 1 and 3,5-bis(methoxymethyl)phenyl trifluoromethanesulfonate (171.0 mg, 0.545 mmol) synthesized in Reference Example 4.

To a solution of 1,4-bis[5-[3,5-bis(methoxymethyl)phenyl]-2-pyridyl]hexahydro-1,4-diazepine (51.9 mg, 0.0892 mmol) in ethanol (5.0 mL) was added 1.0 M hydrochloric acid (0.21 mL, 0.21 mmol), and the reaction mixture was concentrated under reduced pressure. Ethanol (5.0 mL) was added to the residue and the resulting mixture was concentrated under reduced pressure to yield the title compound as a colorless amorphous powder (47.8 mg, yield: 92%).

$^1$H-NMR (CDCl$_3$) (ammonium salt NH$^+$ protons were not observed) δ: 2.36–2.50 (m, 2H), 3.42 (br.s, 12H), 4.02–4.22 (m, 4H), 3.96–4.52 (m, 4H), 4.48 (br.s, 8H), 7.14–7.32 (m, 2H), 7.33 (br.s, 2H), 7.39 (br.s, 4H), 8.09–8.12 (m, 2H), 8.38–8.44 (m, 2H).

EXAMPLE 23

1,4-Bis[5-(2,4,6-trimethoxyphenyl)-2-pyridyl]hexahydro-1,4-diazepine

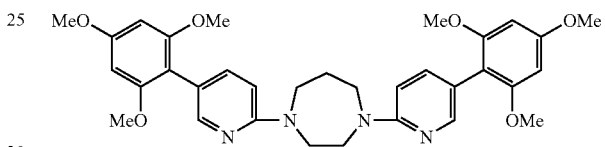

Following the procedure of Example 1, an oil was obtained from 1,4-bis(5-bromo-2-pyridyl)hexahydro-1,4-diazepine (120.0 mg, 0.290 mmol) synthesized in Reference Example 1 and 2,4,6-trimethoxyphenylboronic acid (*Tetrahedron Lett.*, 32, 2229–2232 (1991)) (304.0 mg, 1.45 mmol). Chloroform-hexane was added to the oil, and the resulting precipitate was collected by filtration to yield the title compound as a yellow crystalline powder (melting point: 243.0–247.0° C.) (29.0 mg, yield: 17%).

$^1$H-NMR (CDCl$_3$) δ: 2.16 (tt, J=6.1, 6.1 Hz, 2H), 3.65 (dd, J=6.1, 6.1 Hz, 4H), 3.75 (s, 12H), 3.86 (s, 6H), 3.93 (s, 4H), 6.23 (s, 4H), 6.59 (d, J=8.8 Hz, 2H), 7.48 (dd, J=2.2, 8.8 Hz, 2H), 8.17 (d, J=2.2 Hz, 2H).

EXAMPLE 24

1,4-Bis[5-(2,3,4-trimethoxyphenyl)-2-pyridyl]hexahydro-1,4-diazepine

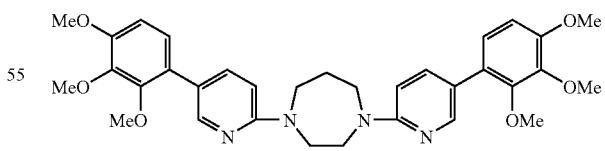

Following the procedure of Example 1, an oil was obtained from 1,4-bis(5-bromo-2-pyridyl)hexahydro-1,4-diazepine (115.0 mg, 0.280 mmol) synthesized in Reference Example 1 and 2,3,4-trimethoxyphenylboronic acid (130.0 mg, 0.620 mmol) synthesized from 2,3,4-trimethoxybromobenzne (*J. Org. Chem.*, 23, 16–17 (1958)) in a similar manner as in Reference Example 2. Chloroform-hexane was added to the oil, and the resulting precipitate was collected by filtration to yield the title compound as a yellow crystalline powder (melting point: 192.0–194.0° C.) (57.0 mg, yield: 35%).

¹H-NMR (CDCl₃) δ: 2.17 (tt, J=6.1, 6.1 Hz, 2H), 3.65 (dd, J=6.1, 6.1 Hz, 4H), 3.72 (s, 6H), 3.89 (s, 6H), 3.92 (s, 6H), 3.96 (s, 4H), 6.60 (d, J=8.8 Hz, 2H), 6.73 (d, J=8.5 Hz 2H), 7.00 (d, J=8.5 Hz, 2H), 7.67 (dd J=2.4, 8.8 Hz, 2H), 8.28 (d, J=2.4 Hz, 2H).

EXAMPLE 25

1,4-Bis[5-(2,3,5-trimethoxyphenyl)-2-pyridyl]hexahydro-1,4-diazepine

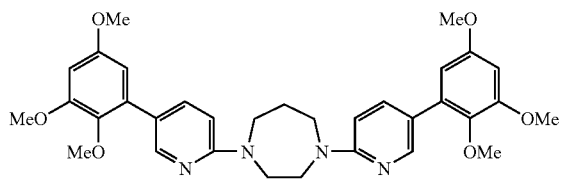

Following the procedure of Example 1, an oil was obtained from 1,4-bis(5-bromo-2-pyridyl)hexahydro-1,4-diazepine (109.0 mg, 0.264 mmol) synthesized in Reference Example 1 and 2,3,5-trimethoxyphenylboronic acid (140.0 mg, 0.660 mmol) synthesized from 1-bromo-2,3,5-trimethoxybenzene (*J. Am. Chem.*, 61, 144–147 (1939)) in a similar manner to that described in Reference Example 2. Methanol-diethyl ether was added to the oil, and the resulting precipitate was collected by filtration to yield the title compound as a pale brown crystalline powder (melting point: 155.0–160.0° C.) (15.0 mg, yield: 10%).

¹H-NMR (CDCl₃) δ: 2.13–2.23 (m, 2H), 3.56 (s, 6H), 3.64–3.70 (m, 4H), 3.81 (s, 6H), 3.88 (s, 6H), 3.97 (s, 4H), 6.43 (d, J=2.7 Hz, 2H), 6.48 (d, J=2.7 Hz, 2H), 6.62 (d, J=9.0 Hz, 2H), 7.76 (dd, J=2.2, 9.0 Hz, 2H), 8.37 (d, J=2.2 Hz, 2H).

EXAMPLE 26

1,4-Bis[5-(3,4,5-trimethoxyphenyl)-2-pyridyl]hexahydro-1,4-diazepine dimethanesulfonate

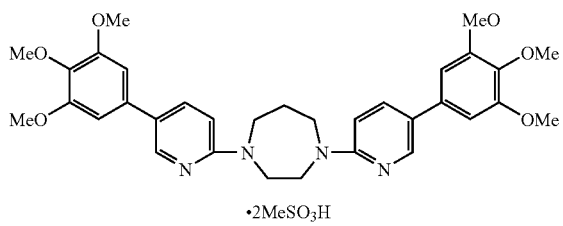

Following the procedure of Example 1, 1,4-bis[5-(3,4,5-triethoxylphenyl)-2-pyridyl]hexahydro-1,4-diazepine was obtained as a colorless oil (22.6 mg, yield: 53%) from 1,4-bis(5-bromo-2-pyridyl)hexahydro-1,4-diazepine (30.0 mg, 0.0730 mmol) synthesized in Referenced Example 1 and 3,4,5-triethoxylphenylboronic acid (45.4 mg, 0.214 mmol).

To a solution of 1,4-bis[5-(3,4,5-triethoxylphenyl)-2-pyridyl]hexahydro-1,4-diazepine (72.4 g, 0.120 mol) in ethanol-chloroform (1:3, 600 mL) was added methanesulfonic acid (24.9 g, 0.258 mol), and the reaction mixture was concentrated under reduced pressure. The residue was recrystallized from methanol-diethyl ether to yield the title compound as a slightly yellow crystalline powder (melting point: 204.0–206.0° C.) (88.2 g, yield: 92%).

¹H-NMR (DMSO-d₆, 120° C.) (ammonium salt NH⁺ protons were not observed) δ: 1.95–2.05 (m, 2H), 2.42 (s, 6H), 3.72 (s, 6H), 3.74–3.77 (m, 4H), 3.82 (s, 12H), 3.98 (s, 4H), 6.79 (s, 4H), 6.92 (d, J=9.0 Hz, 2H), 7.88 (dd, J=2.4, 9.0 Hz, 2H), 8.26 (d, J=2.4 Hz, 2H).

EXAMPLE 27

1,4-Bis[5-(3,4,5-trimethoxyphenyl)-2-pyridyl]hexahydro-1,4-diazepine dimethanesulfonate

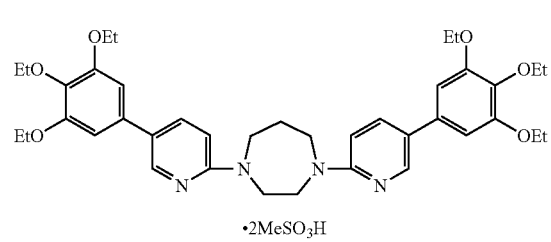

Following the procedure of Example 1, 1,4-bis[5-(3,4,5-triethoxylphenyl)-2-pyridyl]hexahydro-1,4-diazepine was obtained as a colorless oil (77 mg, yield: 48%) from 1,4-bis(5-bromo-2-pyridyl)hexahydro-1,4-diazepine (100.0 mg, 0.240 mmol) synthesized in Reference Example 1 and 3,4,5-triethoxylphenylboronic acid (134.0 mg, 0.530 mmol) synthesized in Reference Example 5.

To a solution of 1,4-bis[5-(3,4,5-triethoxylphenyl)-2-pyridyl]hexahydro-1,4-diazepine (77 mg, 0.115 mmol) in methanol (5.0 mL) was added a 1.0 M aqueous methanesulfonic acid (0.23 mL, 0.23 mmol), and the reaction mixture was concentrated under reduced pressure. Ethanol (5.0 mL) was added to the residue, and the resulting mixture was concentrated under reduced pressure. The residue was recrystallized from methanol-diethyl ether to yield the title compound as a pale yellow crystalline powder (melting point: 235.0–237.0° C.) (74.0 mg, yield: 94%).

¹H-NMR (DMSO-d₆, 120° C.)(ammonium salt NH⁺ protons were not observed) δ: 1.26 (t, J=7.1 Hz, 6H), 1.33 (t, J=7.1 Hz, 12H), 2.01 (tt, J=5.9, 5.9 Hz, 2H) 2.40 (s, 6H), 3.74 (dd, J=5.9, 5.9 Hz, 4H), 3.96 (s, 4H), 3.99 (q, J=7.1 Hz, 4H), 4.08 (q, J=7.1 Hz, 8H), 6.75 (s, 4H), 6.88 (d, J=9.5 Hz, 2H), 7.83 (dd, J=2.4, 9.5 Hz, 2H), 8.23 (d, J=2.4 Hz, 2H).

EXAMPLE 28

1,4-Bis[5-(3,5-diisopropoxy-4-methoxyphenyl)-2-pyridyl]hexahydro-1,4-diazepine

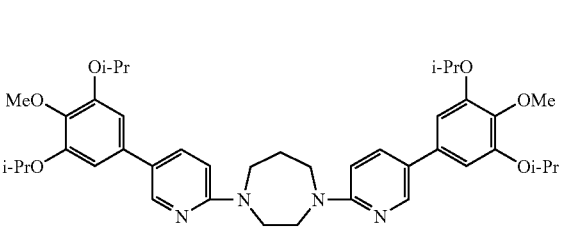

Following the procedure of Example 1, an oil was obtained from 1,4-bis(5-bromo-2-pyridyl)hexahydro-1,4-diazepine (100.0 mg, 0.240 mmol) synthesized in Reference Example 1 and 3,5-diisopropoxy-4-methoxyphenylboronicacid (142.0 mg, 0.530 mmol) synthesized in Reference Example 6. The oil was recrystallized from chloroform-hexane to yield the title compound as slightly brown needles (melting point: 164.0–165.0° C.) (90.0 mg, yield: 53%).

$^1$H-NMR (CDCl$_3$) δ: 1.38 (d, J=5.9 Hz, 24H), 2.16 (tt, J=5.9, 5.9 Hz, 2H), 3.63 (dd, J=5.9, 5.9 Hz, 4H), 3.85 (s, 6H), 3.95 (s, 4H), 4.57 (qq, J=5.9, 5.9 Hz, 4H), 6.61 (d, J=9.0 Hz, 2H), 6.70 (s, 4H), 7.63 (dd, J=2.4, 9.0 Hz, 2H), 8.37 (d, J=2.4 Hz, 2H).

EXAMPLE 29

1,4-Bis[5-(4-isopropoxy-3,5-dimethoxyphenyl)-2-pyridyl]hexahydro-1,4-diazepine dimethanesulfonate

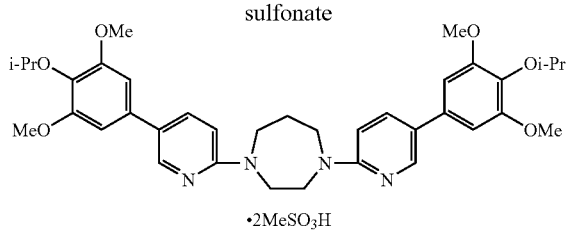

Following the procedure of Example 1, an oil was obtained from 1,4-bis(5-bromo-2-pyridyl)hexahydro-1,4-diazepine (100.0 mg, 0.240 mmol) synthesized in Reference Example 1 and 4-isopropoxy-3,5-dimethoxyphenylboronic acid (127.0 mg, 0.530 mmol) synthesized from methyl syringate in the same manner as described in Reference Example 6, 1,4-bis[5-(4-isopropoxy-3,5-dimethoxy)-2-pyridyl]hexahydro-1,4-benzodiazepine was obtained as a colorless viscous oil (107.0 mg, yield: 69%) by the same procedure described in Example 1.

To a solution of 1,4-bis[5-(4-isopropoxy-3,5-dimethoxy)-2-pyridyl]hexahydro-1,4-benzodiazepine (107.0 mg, 0.166 mmol) was added 1.0 M aqueous methanesulfonic acid (0.35 mL, 0.35 mmol), and the reaction mixture was concentrated under reduced pressure. Ethanol (5.0 mL) was added to the residue, and the resulting mixture was concentrated under reduced pressure. Methanol-diethyl ether was added to the residue, and the resulting precipitate was collected to yield the title compound as a pale yellow crystalline powder (melting point: 192.0–196.0° C.) (100.0 mg, yield: 72%).

$^1$H-NMR (DMSO-d$_6$, 120° C.) (ammonium salt NH$^+$ protons were not observed) δ: 1.21 (d, J=6.1 Hz, 12H), 2.02 (tt, J=5.9, 5.9 Hz, 2H), 2.41 (s, 6H), 3.75 (dd, J=5.9, 5.9 Hz, 4H), 3.80 (s, 12H), 3.97 (s, 4H), 4.30 (qq, J=6.1, 6.1 Hz, 2H), 6.78 (s, 4H), 6.90 (d, J=9.3 Hz, 2H), 7.87 (dd, J=2.4, 9.3 Hz, 2H), 8.27 (d, J=2.4 Hz, 2H).

EXAMPLE 30

1,4-Bis[5-(3-methoxy-4,5-methylenedioxyphenyl)-2-pyridyl]hexahydro-1,4-diazepine dimethanesulfonate

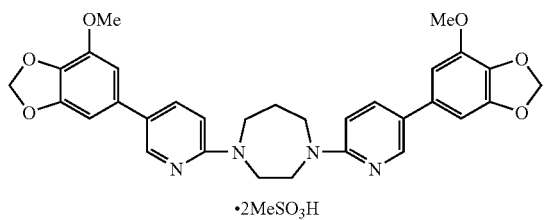

Following the procedure of Example 1, 1,4-bis[5-(3-methoxy-4,5-methylenedioxyphenyl)-2-pyridyl]hexahydro-1,4-diazepine was obtained as a colorless oil (92.0 mg, yield: 71%) from 1,4-bis(5-bromo-2-pyridyl)hexahydro 1,4-diazepine (100.0 mg, 0.240 mmol) synthesized in Reference Example 1 and 3-methoxy-4,5-methylenedioxyphenylboronic acid (103.0 mg, 0.530 mmol) synthesized in Reference Example 7.

To a solution of 1,4-bis[5-(3-methoxy-4,5-methylenedioxyphenyl)-2-pyridyl]hexahydro-1,4-diazepine (92.0 mg, 0.170 mmol) in methanol (5.0 mL) was added a 1.0 M aqueous methanesulfonic acid (0.33 mL, 0.33 mmol), and the reaction mixture was concentrated under reduced pressure. Ethanol (5.0 mL) was added to the residue, and the resulting mixture was concentrated under reduced pressure. Methanol-diethyl ether was added to the residue, and the resulting precipitate was collected to yield the title compound as a pale yellow crystalline powder (melting point: 212.0–215.0° C. (87.0 mg, yield: 68%).

$^1$H-NMR (CDCl$_3$)(data of free base of the title compound) δ: 2.15 (tt, J=6.1, 6.1 Hz, 2H), 3.63 (dd, J=6.1, 6.1 Hz, 4H), 3.94 (s, 4H), 3.95 (s, 6H), 6.00 (s, 4H), 6.60 (d, J=8.8 Hz, 2H), 6.65 (s, 2H), 6.68 (s, 2H), 7.60 (dd, J=2.4, 8.8 Hz, 2H), 8.34 (d, J=2.4 Hz, 2H).

EXAMPLE 31

1,4-Bis[5-(4-hydroxy-3,5 dimethoxyphenyl)-2-pyridyl]hexahydro-1,4-diazepine

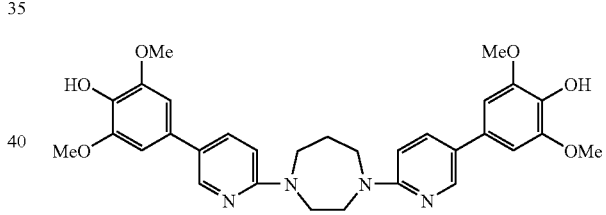

Following the procedure of Example 1, 1,4-bis[5-(4-benzyloxy-3,5-dimethoxyphenyl)-2-pyridyl]hexahydro-1,4-diazepine was obtained as a colorless oil (61.0 mg, yield: 63% ) from 1,4-bis(5-bromo-2-pyridyl)hexahydro-1,4-diazepine (54.0 mg, 0.130 mmol) synthesized in Reference Example 1 and 4-benzyloxy-3,5-dimethoxyphenylboronic acid (80.0 mg, 0.280 mmol) synthesized in Reference Example 8.

To a solution of 1,4-bis[5-(4-benzyloxy-3,5-dimethoxyphenyl)-2-pyridyl]hexahydro-1,4-diazepine (27.0 mg, 0.037 mmol) in methanol (1.0 mL) were added 10% palladium on charcoal (14.0 mg) and ammonium formate (14.0 mg, 0.220 mmol), and the resulting mixture was stirred at 70° C. for 2 hours. Insoluble materials were removed by filtration through Celite, and the filtrate was concentrated under reduced pressure. A solution of the residue in chloroform was washed with water and brine, dried over anhydrous sodium sulfate, and concentrated under reduced pressure. The residue was recrystallized from methanol-chloroform-diethyl ether to yield the title compound as pale brown needles (melting point: 200.0–202.0° C.) (17.0 mg, yield: 85%).

$^1$H-NMR (CDCl$_3$) δ: 2.16 (tt, J=6.3, 6.3 Hz, 2H), 3.63 (dd, J=6.3, 6.3 Hz, 4H), 3.94 (s, 12H), 3.95 (s, 4H), 5.50 (s, 2H), 6.61 (d, J=8.8 Hz, 2H), 6.71 (s, 4H), 7.46 (dd, J=2.2, 8.8 Hz, 2H), 8.37 (d, J=2.2 Hz, 2H).

EXAMPLE 32

1,4-Bis[5-(3-hydroxy-4,5-dimethoxyphenyl)-2-pyridyl]hexahydro-1,4-diazepine dimethanesulfonate

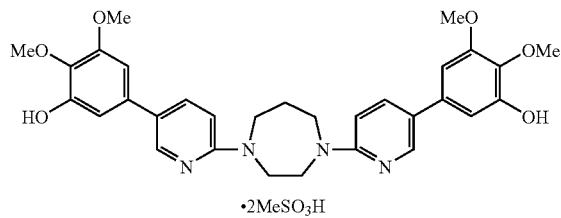

The procedure described in Example 31 was employed. From 1,4-bis(5-bromo-2-pyridyl)hexahydro-1,4-diazepine (115.0 mg, 0.280 mmol) synthesized in Reference Example 1 and 3-benzyloxy-4,5-dimethoxyphenylboronic acid (170.0 mg, 0.590 mmol) synthesized from methyl 3-hydroxy-4,5-dimethoxybenzoate (*Indian J. Chem.*, 21B, 27–29, (1982)) by a similar procedure to that described in Reference Example 8, 1,4-bis[5-(3-benzyloxy-4,5-dimethoxyphenyl)-2-pyridyl]hexahydro-1,4-diazepine was obtained as a colorless viscous oil (173.0 mg, yield: 84%). From 1,4-bis[5-(3-benzyloxy-4,5-dimethoxyphenyl)-2-pyridyl]hexahydro-1,4-diazepine (157.0 mg, 0.210 mmol), 1,4-bis[5-(3-hydroxy-4,5-dimethoxyphenyl)-2-pyridyl]-hexahydro-1,4-diazepine was obtained as a colorless oil (97.0 mg, yield: 84%).

To a solution of 1,4-bis[5-(3-hydroxy-4,5-dimethoxyphenyl)-2-pyridyl]hexahydro-1,4-diazepine (97.0 mg, 0.170 mmol) in methanol (5.0 mL) was added a 1.0 M aqueous methanesulfonic acid (0.35 mL, 0.35 mmol), and the reaction mixture was concentrated under reduced pressure. Ethanol (5.0 mL) was added to the residue, and the resulting mixture was concentrated under reduced pressure. The residue was recrystallized from methanol to yield the title compound as a colorless crystalline powder (melting point: 300.0–301.0° C.) (84.0 mg, yield: 63%).

$^1$H-NMR (DMSO-d$_6$, 120° C.) (neither ammonium salt NH$^+$ protons nor phenol OH protons were observed) δ: 1.96–2.06 (m, 2H), 2.41 (s, 6H), 3.71–3.77 (m, 4H), 3.73 (s, 6H), 3.81 (s, 6H), 3.97 (s, 4H), 6.62 (d, J=2.2 Hz, 2H), 6.65 (d, J=2.2 Hz, 2H), 6.94 (d, J=9.3 Hz, 2H), 7.83 (dd, J=2.4, 9.3 Hz, 2H), 8.17 (d, J=2.4 Hz 2H).

EXAMPLE 33

1,4-Bis[5-(3,5-dimethoxy-4-methylthiophenyl)-2-pyridyl]hexahydro-1,4-diazepine dimethanesulfonate

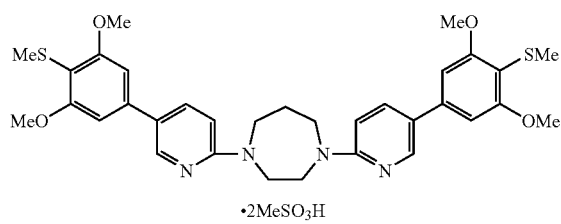

Following the procedure of Example 1, 1,4-bis[5-(3,5-dimethoxy-4-methylthiophenyl)-2-pyridyl]hexahydro-1,4-diazepine was obtained as a colorless oil (72.0 mg, yield: 61%) from 1,4-bis(5-bromo-2-pyridyl)hexahydro-1,4-diazepine (80.0 mg, 0.192 mmol) synthesized in Reference Example 1 and 3,5-dimethoxy-4-methylthiophenylboronic acid (96.0 mg, 0.422 mmol) synthesized in Reference Example 9.

To a solution of 1,4-bis[5-(3,5-dimethoxy-4-methylthiophenyl)-2-pyridyl]hexahydro-1,4-diazepine (72.0 mg, 0.120 mmol) in methanol (5.0 mL) was added a 1.0 M aqueous methanesulfonic acid (0.24 mL, 0.24 mmol), and the reaction mixture was concentrated under reduced pressure. Ethanol (5.0 mL) was added to the residue, and the resulting mixture was concentrated under reduced pressure. Methanol-diethyl ether was added to the residue, and the resulting precipitate was collected to yield the title compound as a pale yellow crystalline powder (melting point: 212.0–217.0° C. (58.0 mg, yield: 61%).

$^1$H-NMR (CDCl$_3$)(ammonium salt NH$^+$ protons were not observed) δ: 2.37–2.40 (m, 2H), 2.38 (s, 6H), 2.91 (s, 6H), 3.92 (s, 12H), 4.00–4.05 (m, 4H), 4.32 (s, 4H), 6.61 (s,4H), 7.40 (d, J=9.4 Hz, 2H), 8.16 (dd, J=2.2, 9.4 Hz, 2H), 8.46 (d, J=2.2 Hz, 2H).

EXAMPLE 34

1,4-Bis[5-(4-amino-3,5-dimethoxyphenyl)-2-pyridyl]hexahydro-1,4-diazepine tetrahydrochloride

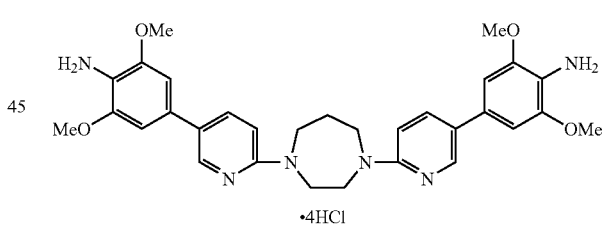

Following the procedure of Example 17, 1,4-bis[5-(4-benzyloxycarbonylamino-3,5-dimethoxyphenyl)-2-pyridyl]hexahydro-1,4-diazepine was obtained as a colorless oil (120.0 mg, yield: 26%) from 1,4-bis(5-bromo-2-pyridyl)hexahydro-1,4-diazepine (228.0 mg, 0.550 mmol) synthesized in Reference Example 1 and 4-benzyloxycarbonylamino-1-bromo-3,5-dimethoxybenzene (450.0 mg, 1.24 mmol).

To a solution of 1,4-bis[5-(4-benzyloxycarbonylamino-3, 5-dimethoxyphenyl)-2-pyridyl]hexahydro-1,4-diazepine (120.0 mg, 0.140 mmol) in acetic acid (2.0 mL) was added 10% palladium on charcoal (24.0 mg), and the resulting mixture was stirred at 50° C. for 1.5 hours under hydrogen. Insoluble materials were removed by filtration through Celite, and the filtrate was concentrated under reduced pressure. A solution of the residue in chloroform was washed with saturated aqueous sodium hydrogencarbonate and brine, dried over anhydrous sodium sulfate, and concentrated under reduced pressure. To a solution of the residue in chloroform (5.0 mL) a 4.0 M solution of hydrogen chloride in ethyl acetate (0.14 mL, 0.56 mmol), and the resulting mixture was concentrated under reduced pressure. Ethanol (5.0 mL) was added to the residue, and the resulting mixture was concentrated under reduced pressure. Diethyl ether was added to the residue, and the resulting precipitate was collected by filtration to yield the title compound as a pale brown amorphous powder (84.0 mg, yield: 82%).

$^1$H-NMR (CDCl$_3$) (data of the free base of the title compound; amine NH$_2$ protons were not observed) δ: 2.12–2.22 (m, 2H), 3.59–3.66 (m, 4H), 3.90 (s, 12H), 3.94 (s, 4H), 6.60 (d, J=8.8 Hz, 2H), 6.67 (s, 4H), 7.64 (d, J=2.0, 8.8 Hz, 2H), 8.38 (d, J=2.0 Hz, 2H).

EXAMPLE 35

1,4-Bis[5-(4-dimethylamino-3,5-dimethoxyphenyl)-2-pyridyl]hexahydro-1,4-diazepine

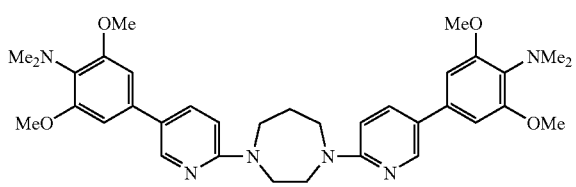

Following the procedure of Example 17, crude crystals were obtained from 1,4-bis(5-bromo-2-pyridyl)hexahydro-1,4-diazepine (210.0 mg, 0.510 mmol) synthesized in Reference Example 1 and 1-bromo-4-dimethylamino-3,5-dimethoxybenzene (300.0 mg, 1.14 mmol) synthesized from 4-bromo-2,6-dimethoxyaniline (Z. Naturforsch., B24(5), 524–527(1969)). The crude crystals were recrystallized from methanol to yield the title compound as a yellow crystalline powder (melting point: 211.0–213.0° C.) (36.0 mg, yield: 12%).

$^1$H-NMR (CDCl$_3$) δ: 2.16 (tt, J=6.3, 6.3 Hz, 2H), 2.84 (s, 12H), 3.64 (dd, J=6.3, 6.3 Hz, 4H), 3.89 (s, 12H), 3.96 (s, 4H), 6.61 (d, J=9.0 Hz, 2H), 6.66 (s, 4H), 7.66 (dd, J=2.2, 9.0 Hz, 2H), 8.41 (d, =2.2 Hz, 2H).

EXAMPLE 36

1,4-Bis[5-[3,5-dimethoxy-4-(1-pyrrolidinyl)phenyl]-2-pyridyl]hexahydro-1,4-diazepine

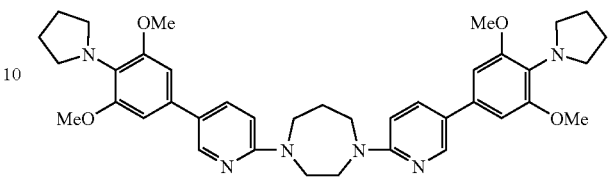

Following the procedure of Example 17, crude crystals were obtained from 1,4-bis(5-bromo-2-pyridyl)hexahydro-1,4-diazepine (280.0 mg, 0.680 mmol) synthesized in Reference Example 1 and 1-bromo-3,5-dimethoxy-4-(1-pyrrolidinyl)benzene (436.0 mg, 1.52 mmol) synthesized from 4-bromo-2,6-dimethoxyaniline (Z. Naturforsch., B24(5), 524–527(1969)). The crude crystals were recrystallized from methanol to yield the title compound as a pale brown crystalline powder (melting point: 204.0–207.0° C.) (40.0 mg, yield: 9%).

$^1$H-NMR (CDCl$_3$) δ: 1.91–1.97 (m, 8H), 2.16 (tt, J=6.3, 6.3 Hz, 2H), 3.26–3.33 (m, 8H), 3.64 (dd, J=6.3, 6.3 Hz, 4H), 3.87 (s, 12H), 3.95 (s, 4H), 6.61 (d, J=8.8 Hz, 2H), 6.69 (s, 4H), 7.66 (dd, J=2.2, 8.8 Hz, 2H), 8.41 (d, J=2.2 Hz, 2H).

EXAMPLE 37

1,4-Bis[5-(4-methanesulfonylamino-3,5-dimethoxyphenyl)-2-pyridyl]hexahydro-1,4-diazepine

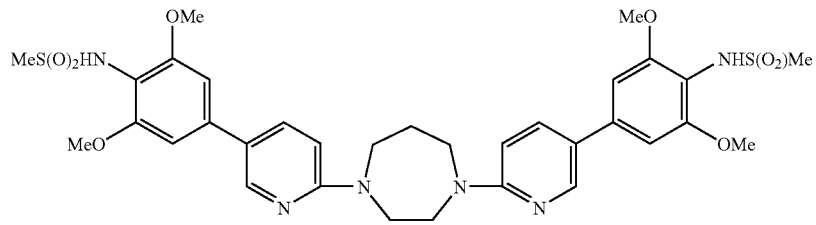

To a solution of 1,4-bis[5-(4-amino-3,5-dimethoxyphenyl)-2-pyridyl]hexahydro-1,4-diazepine tetrahydrochloride (40.0 mg, 0.0570 mmol), which was synthesized in Example 34, in pyridine (1.0 mL) was added methanesulfonyl chloride (30.0 mg, 0.260 mmol). The reaction mixture was stirred for 15 minutes, and concentrated under reduced pressure. A solution of the residue in methanol-chloroform (1:10) was washed with saturated aqueous sodium hydrogencarbonate and brine, dried over anhydrous sodium sulfate, and concentrated under reduced pressure. The residue was recrystallized from chloroform-hexane to yield the title compound as a pale brown crystalline powder (melting point: 235.0–239.0° C.) (28.0 mg, yield: 68%).

$^1$H-NMR (CDCl$_3$) δ: 2.10–2.22 (m, 2H), 3.27 (s, 6H), 3.60–3.70 (m, 4H), 3.93 (s, 12H), 3.97 (s, 4H), 6.13 (s, 2H), 6.63 (d, J=8.8 Hz, 2H), 6.70 (s, 4H), 7.65 (dd, J=2.2, 8.8 Hz, 2H), 8.39 (d, J=2.2 Hz, 2H).

EXAMPLE 38

1,4-Bis[5-(4-fluoro 3,5-dimethoxyphenyl)-2-pyridyl]hexahydro-1,4-diazepine

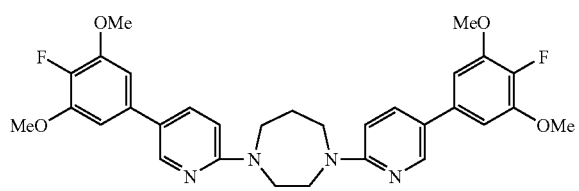

Following the procedure of Example 1, the title compound was obtained as a pale yellow amorphous powder (138.9 mg, yield: 93%) from 1,4-bis(5-bromo-2-pyridyl)hexahydro-1,4-diazepine (110.0 mg, 0.270 mmol) synthesized in Reference Example 1 and 4-fluoro-3,5-dimethoxyphenylboronic acid (160.0 mg, 0.800 mmol) synthesized from 1-bromo-4-fluoro-3,5-dimethoxybenzene (JP 10-87543A) synthesized by a similar procedure to that described in Reference Example 2.

$^1$H-NMR (CDCl$_3$) δ: 2.16 (tt, J=6.0, 6.03 Hz, 2H), 3.64 (dd, J=6.0, 6.0 Hz, 4H), 3.93 (s, 12H), 3.95 (s, 4H), 6.62 (d, J=9.0 Hz, 2H), 6.71 (d, $^4$J$_{HF}$=6.0 Hz, 4H), 7.63 (dd, J=3.0, 9.0 Hz, 2H), 8.36 (d, J=3.0 Hz, 2H).

EXAMPLE 39

1,4-Bis[5-(4-chloro-3,5-dimethoxyphenyl)-2-pyridyl]hexahydro-1,4-diazepine dimethanesulfonate

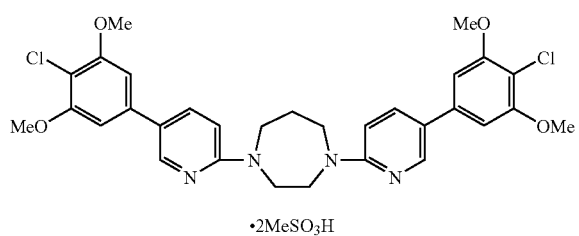

Following the procedure of Example 1, 1,4-bis[5-(4-chloro-3,5-dimethoxyphenyl)-2-pyridyl]hexahydro-1,4-diazepine was obtained as a colorless crystalline powder (98.0 mg, yield: 82%) from 1,4-bis(5-bromo-2-pyridyl)hexahydro-1,4-diazepine (82.0 mg, 0.200 mmol) synthesized in Reference Example 1 and 4-chloro-3,5-dimethoxyphenylboronic acid (130.0 mg, 0.600 mmol) synthesized in Reference Example 10.

To a solution of 1,4-bis[5-(4-chloro-3,5-dimethoxyphenyl)-2-pyridyl]hexahydro-1,4-diazepine (130.0 mg, 0.210 mmol) in methanol (5.0 mL) was added a 1.0 M aqueous methanesulfonic acid (0.45 mL, 0.45 mmol), and the reaction mixture was concentrated under reduced pressure. Ethanol (5.0 mL) was added to the residue, and the resulting mixture was concentrated under reduced pressure. The residue seas recrystallized from methanol-chloroform-diethyl ether to yield the title compound as a colorless crystalline powder (melting point: 279.0–282.0° C.)(138.0 mg, yield: 83%).

$^1$H-NMR (DMSO-d$_6$, 120° C.) (ammonium salt NH$^+$ protons were not observed) δ: 2.03 (tt, J=5.8, 5.8 Hz, 2H), 2.46 (s, 6H), 3.77(dd, J=5.8, 5.8 Hz, 4H), 3.88 (s, 12H), 3.99 (s, 4H), 6.88 (s, 4H), 6.95 (d, J=9.0 Hz, 2H), 7.94 (dd, J=2.6, 9.0 Hz, 2H), 8.35 (d, J=2.6 Hz, 2H).

EXAMPLE 40

1,4-Bis[5-(4-cyano-3,5-dimethoxyphenyl)-2-pyridyl]hexahydro-1,4-diazepine

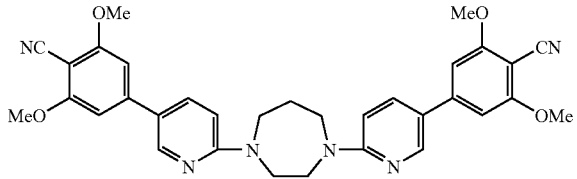

Following the procedure of Example 1, an oil was obtained from 1,4-bis(5-bromo-2-pyridyl)hexahydro-1,4-diazepine (124.0 mg, 0.300 mmol) synthesized in Reference Example 1 and 4-cyano-3,5-dimethoxyphenylboronic acid (191.0 mg, 0.660 mmol) synthesized in Reference Example 11. Chloroform-hexane was added to the oil, and the resulting precipitate was collected by filtration to yield the title compound as a pale brown crystalline powder (melting point: ≧300° C.) (16.0 mg, yield: 9%).

$^1$H-NMR (CDCl$_3$) δ: 2.16 (tt, J=6.1, 6.1 Hz, 2H), 3.66 (dd, J=6.1, 6.1 Hz, 4H), 3.96 (s, 12H), 3.97 (s, 4H), 6.64 (d, J=8.9 Hz, 2H), 6.65 (s, 4H), 7.68 (dd, J=2.4, 8.9 Hz, 2H), 8.44 (d, J=2.4 Hz, 2H).

EXAMPLE 41

1,4-Bis[5-(3,5-dimethoxy-4-methylphenyl)-2-pyridyl]hexahydro-1,4-diazepine dimethanesulfonate

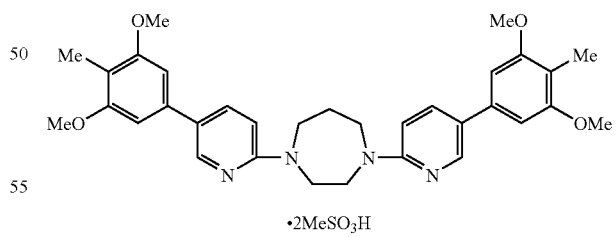

Following the procedure of Reference Example 2,3,5-dimethoxy-4-methylphenylboronic acid was synthesized from 1-iodo-3,5-dimethoxy-4-methylbenzene which had been synthesized as an intermediate in Reference Example 11.

Following the procedure of Example 1, 1,4-bis[5-(3,5-dimethoxy-4-methylphenyl)-2-pyridyl]hexahydro-1,4-diazepine was obtained as a pale yellow oil (77.0 mg, yield: 58%) from 1,4-bis(5-bromo-2-pyridyl)hexahydro-1,4-diazepine (100.0 mg, 0.240 mmol) synthesized in Reference Example 1 and 3,5-dimethoxy-4-methylphenylboronic acid (103.0 mg, 0.530 mmol).

To a solution of 1,4-bis[5-(3,5-dimethoxy-4-methylphenyl)-2-pyridyl]hexahydro-1,4-diazepine (77.0 mg, 0.140 mmol) in methanol (5.0 mL) was added a 1.0 M aqueous methanesulfonic acid (0.28 mL, 0.28 mmol), and the reaction mixture was concentrated under reduced pressure. Ethanol (5.0 mL) was added to the residue, and the resulting mixture was concentrated under reduced pressure. The residue was recrystallized from methanol-chloroform-diethyl ether to yield the title compound as a pale yellow crystalline powder (melting point: 235.0–237.0° C. (67.0 mg, yield: 64%).

$^1$H-NMR (CDCl$_3$) (data of the free base of the title compound) δ: 2.12 (s, 6H), 2.17 (tt, J=6.0, 6.0 Hz, 2H), 3.64 (dd, J=6.0, 6.0 Hz, 4H), 3.87 (s, 12H), 3.96 (s, 4H), 6.62 (d, J=9.0 Hz, 2H), 6.66 (s, 4H), 7.68 (dd, J=2.2, 9.0 Hz, 2H), 8.42 (d, J=2.2 Hz, 2H).

EXAMPLE 42

1,4-Bis[5-(4-hydroxymethyl-3,5-dimethoxyphenyl)-2-pyridyl]hexahydro-1,4-diazepine

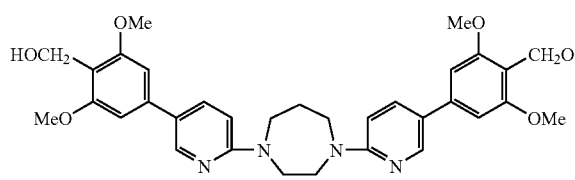

Following the procedure of Example 17, an oil (192.0 mg) containing 1,4-bis[5-[4-(t-butyldimethylsiloxy)methyl-3,5-dimethoxyphenyl]-2-pyridyl]hexahydro-1,4-diazepine was obtained from 1,4-bis(5-bromo-2-pyridyl)hexahydro-1,4-diazepine (128.0 mg, 0.310 mmol) synthesized in Reference Example 1 and 4-(t-butyldimethylsiloxy)methyl-3,5-dimethoxyphenyl trifluoromethanesulfonate (400.0 mg, 0.929 mmol) synthesized in Reference Example 12.

To a solution of the oil (192.0 mg), which had been obtained by the above procedure, in methanol (9.5 mL) was added 46% hydrofluoric acid (0.50 mL), and the resulting mixture was stirred at room temperature for 30 minutes. A 5.0 M aqueous sodium hydroxide (5.0 mL) was added to the reaction mixture. The mixture was extracted with chloroform, and the organic layer was concentrated under reduced pressure. The residue was purified by column chromatography on silica gel to give an oil. The oil was recrystallized from methylene chloride-diethyl ether-hexane to yield the title compound as a slightly yellow crystalline powder (melting point: ≧300.0° C.) (29.0 mg, yield: 16% based on 1,4-bis(5-bromo-2-pyridyl)-hexahydro-1,4-diazepine).

$^1$H-NMR (CDCl$_3$) δ: 2.14–2.28 (m, 2H), 2.41 (br.t, J=5.9 Hz, 2H), 3.89 (s, 12H), 3.55–4.15 (m, 8H), 4.80 (br.d, J=5.9 Hz, 4H), 6.64 (br.d, J=8.8 Hz, 2H), 6.67 (s, 4H), 7.69 (br.d, J=8.8 Hz, 2H), 8.42 (br.s, 2H).

EXAMPLE 43

1,4-Bis[5-(4-ethoxycarbonyl-3,5-dimethoxyphenyl)-2-pyridyl]hexahydro-1,4-diazepine

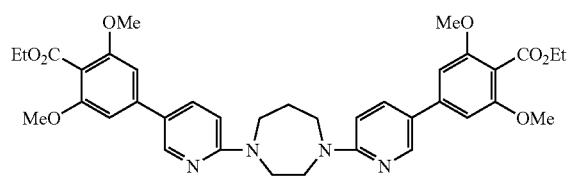

Following the procedure of Example 17, an oil was obtained from 1,4-bis(5-bromo-2-pyridyl)hexahydro-1,4-diazepine (243.0 mg, 0.590 mmol) synthesized in Reference Example 1 and 4-ethoxycarbonyl-1-iodo-3,5-dimethoxybenzene (595.0 mg, 0.929 mmol) synthesized in Reference Example 13. The oil was recrystallized from methylene chloride-diethyl ether-hexane to yield the title compound as a pale brown crystalline powder (melting point: 244.0–245.0° C.) (75.1 mg, yield: 19%).

$^1$H-NMR (CDCl$_3$) δ: 1.38 (br.t, J=7.0 Hz, 6H), 2.12–2.25 (m, 2H), 3.87 (s, 12H), 3.60–4.05 (m, 8H), 4.40 (br.q, J=7.0 Hz, 4H), 6.62 (br.d, J=8.8 Hz, 2H), 6.66 (s, 4H), 7.66 (br.dd, J=2.4, 8.8 Hz, 2H), 8.40 (br.d, J=2.4 Hz, 2H).

EXAMPLE 44

1,4-Bis[5-(4-carboxy-3,5-dimethoxyphenyl)-2-pyridyl]hexahydro-1,4-diazepine ditrifluoroacetate

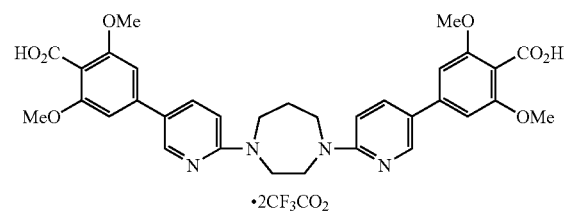

Following the procedure of Example 1, 1,4-bis[5-(4-t-butoxycarbonyl-3,5-dimethoxyphenyl)-2-pyridyl]hexahydro-1,4-diazepine was obtained as a pale yellow oil (27.0 mg, yield: 25%) from 1,4-bis(5-bromo-2-pyridyl)hexahydro-1,4-diazepine (62.0 mg, 0.150 mmol) synthesized in Reference Example 1 and 4-t-butoxycarbonyl-3,5-dimethoxyphenylboronic acid (102.0 mg, 0.360 mmol) synthesized in Reference Example 14.

To a solution of 1,4-bis[5-(4-t-butoxycarbonyl-3,5-dimethoxyphenyl)-2-pyridyl]hexahydro-1,4-diazepine (27.0 mg, 0.037 mmol) in chloroform (4.0 mL) was added trifluoroacetic acid (0.3 mL), and the resulting mixture was stirred for 30 minutes. The reaction mixture was concentrated under reduced pressure. Methanol-chloroform-diethyl ether-hexane was added to the residue and the resulting precipitate was collected to yield the title compound as a pale yellow crystalline powder [melting point: 164.5° C. (decomposed)] (22.6 mg, yield: 72%).

$^1$H-NMR [CD$_3$OD-CDCl$_3$(1:10)] (neither ammonium salt NH$^+$ protons nor carboxylic acid CO$_2$H protons were observed) δ: 2.12–2.28 (m, 2H), 3.89 (br.s, 12H), 3.70–4.07

(m, 8H), 6.69 (br.s, 4H), 6.82 (br.d, J=9.8 Hz, 2H), 7.82 (br.d, J=9.8 Hz, 2H), 8.34 (br.s, 2H).

EXAMPLE 45

1,4-Bis[5-(4-acetyl-3,5-dimethoxyphenyl)-2-pyridyl]hexahydro-1,4-diazepine dimethanesulfonate

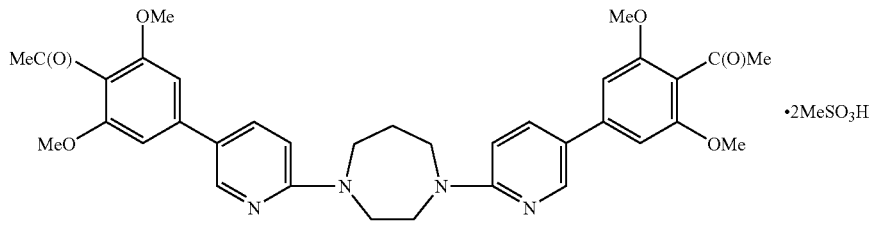

Following the procedure of Example 17, 1,4-bis[5-(4-acetyl-3,5-dimethoxyphenyl)-2-pyridyl]hexahydro-1,4-diazepine was obtained as colorless crystalline powder (162.0 mg, yield: 53%) from 1,4-bis(5-bromo-2-pyridyl)-hexahydro-1,4-diazepine (206.0 mg, 0.500 mmol) synthesized in. Reference Example 1 and 4-acetyl-3,5-dimethoxyphenyl trifluoro-methanesulfonate (410.0 mg, 1.250 mmol) synthesized in Reference Example 15.

To a solution of 1,4-bis[5-(4-acetyl-3,5-dimethoxyphenyl)-2-pyridyl]hexahydro-1,4-diazepine (80.0 mg, 0.130 mmol) in chloroform (5.0 mL), a 1.0 M solution of methanesulfonic acid in methanol (0.33 mL, 0.33 mmol) was added, and the reaction mixture was concentrated under reduced pressure. The residue was recrystallized from methanol-diethyl ether to yield the title compound as a colorless crystalline powder (melting point: 236.0–238.0° C.) (94.8 mg, yield: 90%).

$^1$H-NMR (CDCl$_3$)(ammonium salt NH$^+$ protons were not observed) δ: 2.34–2.42 (m, 2H), 2.48 (s, 6H), 2.91 (s, 6H), 3.84 (s, 12H), 3.98–4.07 (m, 4H), 4.31 (s, 4H), 6.61 (s, 4H), 7.41 (br.d, J=9.4 Hz, 2H), 8.15 (br.d, J=9.4 Hz, 2H), 8.43 (br.s, 2H).

EXAMPLE 46

1,4-Bis[5-(4-methoxy-3,5-dimethylphenyl)-2-pyridyl]hexahydro-1,4-diazepine dimethanesulfonate

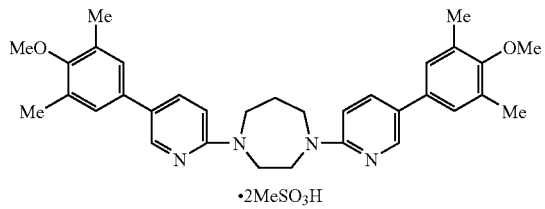

Following the procedure of Example 1, 1,4-bis[5-(4-methoxy-3,5-dimethylphenyl)-2-pyridyl]hexahydro-1,4-diazepine was obtained as a colorless crystalline powder (130.0 mg, yield: 82%) from 1,4-bis(5-bromo-2-pyridyl) hexahydro-1,4-diazepine (123.0 mg, 0.300 mmol) synthesized in Reference Example 1 and 4-methoxy-3,5-dimethylphenylboronic acid (152.0 mg, 0.900 mmol) synthesized from 1-bromo-4-methoxy-3,5-dimethylbenzene (*Tetrahedron Lett.*, 30, 735–738(1989)) by a similar procedure as in Reference Example 2.

To a solution of 1,4-bis[5-(4-methoxy-3,5-dimethylphenyl)-2-pyridyl]hexahydro-1,4-diazepine (126.0 mg, 0.240 mmol) in methanol (10 mL) was added a 1.0 M aqueous methanesulfonic acid (0.50 mL, 0.50 mmol), and the reaction mixture was concentrated under reduced pressure. Ethanol (10 mL) vas added to the residue, and the resulting mixture was concentrated under reduced pressure. The residue was recrystallized from ethanol-diethyl ether-hexane to yield the title compound as a colorless crystalline powder (melting point: 250.0–253.0° C.) (157.0 mg, yield: 91%).

$^1$H-NMR (DMSO-d$_6$, 120° C.) (ammonium salt NH$^+$ protons were not observed) δ: 2.01 (tt, J=5.8, 5.8 Hz, 2H), 2.24 (s, 12H), 2.45 (s, 6H), 3.68 (s, 6H), 3.77 (dd, J=5.8, 5.8 Hz, 4H), 4.00 (s, 4H), 6.98 (d, J=9.0 Hz, 2H), 7.14 (s, 4H), 7.86 (dd, J=2.4, 9.0 Hz, 2H), 8.15 (d, J=2.4 Hz, 2H).

EXAMPLE 47

1,4-Bis[5-(3-formyl-2-furyl)-2-pyridyl]hexahydro-1,4-diazepine

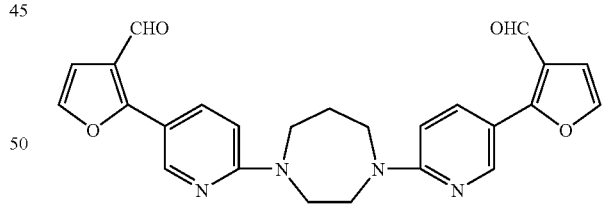

Following the procedure of Example 1, the title compound was obtained as a brown amorphous powder (8.0 mg, yield: 9%) from 1,4-bis(5-bromo-2-pyridyl)hexahydro-1,4-diazepine (82.0 mg, 0.200 mmol) synthesized in Reference Example 1 and 3-formylfuran-2-boronic acid (62.0 mg, 0.440 mmol).

$^1$H-NMR (CDCl$_3$) δ: 2.15 (tt, J=6.0, 6.0 Hz, 2H), 3.68 (dd, J=6.0, 6.0 Hz, 4H), 3.99 (s, 4H), 6.65 (d, J=9.0 Hz, 2H), 6.87 (d, J=2.1 Hz, 2H), 7.42 (d, J=2.1 Hz, 2H), 7.87 (dd, J=2.4, 9.0 Hz, 2H), 8.57 (d, J=2.4 Hz, 2H), 10.04 (s, 2H).

EXAMPLE 48

1,4-Bis[5-(3-thienyl)-2-pyridyl]hexahydro-1,4-diazepine

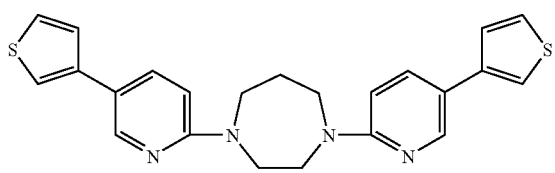

Following the procedure of Example 1, crude crystals were obtained from 1,4-bis(5-bromo-2-pyridyl)hexahydro-1,4-diazepine (82.0 mg, 0.200 mmol) synthesized in Reference Example 1 and thiophene-3-boronic acid (56.0 mg, 0.44 mmol). Methanol-chloroform-diethyl ether was added to the crude crystals and the resulting precipitate novas collected by filtration to yield the title compound as brown needles (melting-point: 234.0–236.0° C.) (35.0 mg, yield: 42%).

$^1$H-NMR (CDCl$_3$) δ: 2.14 (tt, J=6.3, 6.3 Hz, 2H), 3.61 (dd, J=6.3, 6.3 Hz, 4H), 3.93 (s, 4H), 6.58 (d, J=9.0 Hz, 2H), 7.28–7.33 (m, 4H), 7.36–7.39 (m, 2H), 7.66 (dd, J=2.4, 9.0 Hz, 2H), 8.44 (d, J=2.4 Hz, 2H).

EXAMPLE 49

1,4-Bis[5-(2-formyl-3-thienyl)-2-pyridyl]hexahydro-1,4-diazepine

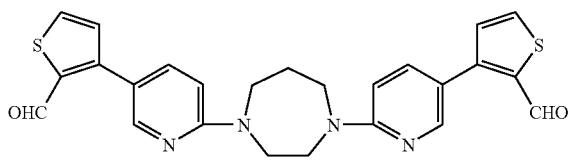

Following the procedure of Example 1, the title compound was obtained as a pale yellow amorphous powder (71.0 mg, yield: 74%) from 1,4-bis(5-bromo-2-pyridyl)hexahydro-1,4-diazepine (82.0 mg, 0.200 mmol) synthesized in Reference Example 1 and 2-formylthiophene-3-boronic acid (69.0 mg, 0.44 mmol).

$^1$H-NMR (DMSO-d$_6$, 120° C.) δ: 2.02 (tt, J=6.0, 6.0 Hz, 2H), 3.71 (dd, J=6.0, 6.0 Hz, 4H), 3.94 (s, 4H), 6.77 (d, J=8.7 Hz, 2H), 7.27 (d, J=4.8 Hz, 2H), 7.65 (dd, J=2.6, 8.7 Hz, 2H), 7.97 (dd, J=1.2, 4.8 Hz, 2H), 8.25 (d, J=2.6 Hz, 2H), 9.78 (d, J=1.2 Hz, 2H).

EXAMPLE 50

1,4-Bis[5-(2-thienyl)-2-pyridyl]hexahydro-1,4-diazepine

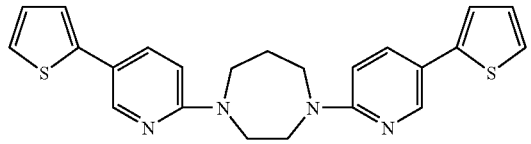

Following the procedure of Example 1, crude crystals were obtained from 1,4-bis(5-bromo-2-pyridyl)hexahydro-1,4-diazepine (82.0 mg, 0.200 mmol) synthesized in Reference Example 1 and thiophene-2-boronic acid (56.0 mg, 0.44 mmol). Methanol-chloroform-diethyl ether was added to the crude crystals and the resulting precipitate was collected by filtration to yield the title compound as a brown crystalline powder (melting point: 170.0–172.0° C.)(21.0 mg, yield: 25%).

$^1$H-NMR (DMSO-d$_6$, 120° C.) δ: 1.99 (tt, J=6.0, 6.0 Hz, 2H), 3.65 (dd, J=6.0, 6.0 Hz, 4H), 3.88 (s, 4H), 6.91 (d, J=9.0 Hz, 2H), 7.03 (dd, J=3.4, 5.1 Hz, 2H), 7.19 (dd, J=1.2, 3.4 Hz, 2H), 7.30 (dd, J=1.2, 5.1 Hz, 2H), 7.65 (dd, J=2.6, 9.0 Hz, 2H), 8.31 (d, J=2.6 Hz, 2H).

EXAMPLE 51

1,4-Bis[5-(5-acetyl-2-thienyl)-2-pyridyl]hexahydro-1,4-diazepine

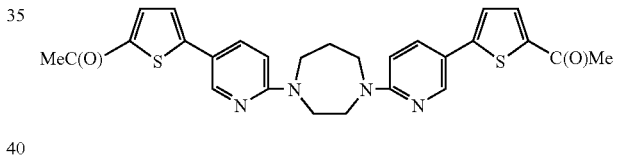

Following the procedure of Example 1, the title compound was obtained as a yellow amorphous powder (12.0 mg, yield: 11%) from 1,4-bis(5-bromo-2-pyridyl)hexahydro-1,4-diazepine (82.0 mg, 0.200 mmol) synthesized in Reference Example 1 and 5-acetylthiophene-2-boronic acid (75.0 mg, 0.44 mmol).

$^1$H-NMR (DMSO-d$_6$, 120° C.) δ: 1.99 (tt, J=6.0, 6.0 Hz, 2H), 2.46 (s, 6H), 3.67 (dd, J=6.0, 6.0 Hz, 4H), 3.91 (s, 4H), 6.72 (d, J=9.0 Hz, 2H), 7.29 (d, J=4.1 Hz, 2H), 7.72 (dd, J=2.4, 9.0 Hz, 2H), 7.73 (d, J=4.1 Hz, 2H), 8.42 (d, J=2.4 Hz, 2H).

EXAMPLE 52

1,4-Bis[5-(3-pyridyl)-2-pyridyl]hexahydro-1,4-diazepine

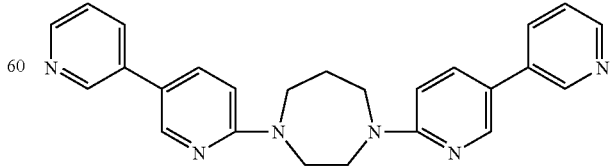

Following the procedure of Example 1, crude crystals were obtained from 1,4-bis(5-bromo-2-pyridyl)hexahydro- 1,4-diazepine (82.0 mg, 0.200 mmol) synthesized in Reference Example 1 and pyridine-3-boronic acid (54.0 mg, 0.44 mmol). The crude crystals were recrystallized from chloroform-hexane to yield the title compound as colorless flakes (melting point: 210.0–211.0° C.) (38.0 mg, yield: 45%).

$^1$H-NMR (CDCl$_3$) δ: 2.17 (tt, J=6.0, 6.0 Hz, 2H), 3.65 (dd, J=6.0, 6.0 Hz, 4H), 3.97 (s, 4H), 6.66 (d, J=9.0 Hz, 2H), 7.33 (dd, J=4.8, 7.8 Hz, 2H), 7.68 (dd, J=2.4, 9.0 Hz, 2H), 7.80 (ddd, J=1.7, 2.1, 7.8 Hz, 2H), 8.41 (d, J=2.4 Hz, 2H), 8.53 (dd, J=1.7, 4.8 Hz, 2H), 8.78 (d, J=2.1 Hz, 2H).

EXAMPLE 53

1,4-Bis[5-(2-benzo[b]furyl)-2-pyridyl]hexahydro-1,4-diazepine

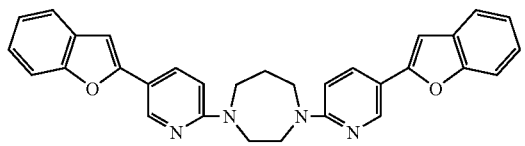

Following the procedure of Example 1, crude crystals were obtained from 1,4-bis(5-bromo-2-pyridyl)hexahydro-1,4-diazepine (82.0 mg, 0.200 mmol) synthesized in Reference Example 1 and benzo[b]furan-2-boronic acid (71.0 mg, 0.44 mmol). Methanol-chloroform-diethyl ether was added to the crude crystals and the resulting precipitate was collected by filtration to yield the title compound as a colorless crystalline powder [melting point: 245.0° C. (decomposed)] (17.0 mg, yield: 17%).

$^1$H-NMR (DMSO-d$_6$, 120° C.) δ: 2.02 (tt, J=6.0, 6.0 Hz, 2H), 3.70 (dd, J=6.0, 6.0 Hz, 4H), 3.94 (s, 4H), 6.77 (d, J=9.0 Hz, 2H), 6.97–6.99 (m, 2H), 7.14–7.23 (m, 4H), 7.44–7.56 (m, 4H), 7.87 (dd, J=2.4, 9.0 Hz, 2H), 8.57 (d, J=2.4 Hz, 2H).

EXAMPLE 54

1,4-Bis[5-(2-benzo[b]thienyl)-2-pyridyl]hexahydro-1,4-diazepine

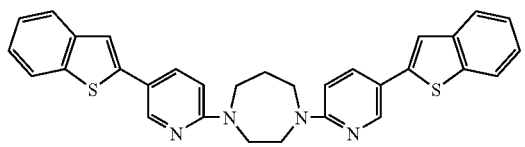

Following the procedure of Example 1, crude crystals were obtained from 1,4-bis(5-bromo-2-pyridyl)hexahydro-1,4-diazepine (82.0 mg, 0.200 mmol) synthesized in Reference Example 1 and benzo[b]thiophene-2-boronic acid (78.0 mg, 0.44 mmol). Methanol-chloroform-diethyl ether was added to the crude crystals and the resulting precipitate was collected by filtration to yield the title compound as a colorless crystalline powder [melting point: 246.0° C. (decomposed)] (41.0 mg, yield: 39%).

$^1$H-NMR (DMSO-d$_6$, 120° C.) δ: 2.01 (tt, J=6.0, 6.0 Hz, 2H), 3.69 (dd, J=6.0, 6.0 Hz, 4H), 3.92 (s, 4H), 6.75 (d, J=9.0 Hz, 2H), 7.20–7.35 (m, 4H), 7.49 (s, 2H), 7.67–7.75 (m, 2H), 7.77 (dd, J=2.4, 9.0 Hz, 2H), 7.80–7.84 (m, 2H), 8.43 (d, J=2.4 Hz, 2H).

EXAMPLE 55

1,4-Bis[5-(3,4,5-trimethoxyphenyl)-2-pyridyl]piperazine dimethanesulfonate

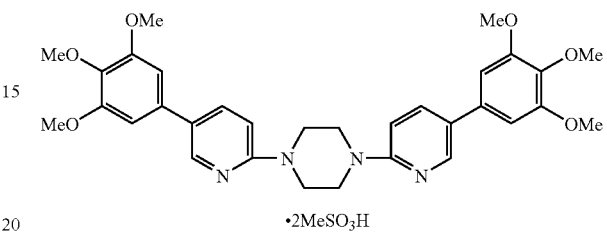

Following the procedure of Example 1, 1,4-bis[5-(3,4,5-trimethoxyphenyl)-2-pyridyl]piperazine was obtained as a colorless crystalline powder (147.0 mg, yield: 52%) from 1,4-bis(5-bromo-2-pyridyl)piperazine (199.0 mg, 0.500 mmol) synthesized in a similar manner to that described in Reference Example 1 and 3,4,5-trimethoxyphenylboronic acid (318.0 mg, 1.50 mmol).

To a solution of 1,4-bis[5-(3,4,5-trimethoxyphenyl)-2-pyridyl]piperazine (147.0 mg, 0.257 mmol) in methylene chloride (5.0 mL) was added a 1.0 M solution of methanesulfonic acid in methanol (0.54 mL, 0.54 mmol), and the reaction mixture was concentrated under reduced pressure. The residue was recrystallized from methylene chloride-diethyl ether to yield the title compound as a pale yellow crystalline powder (melting point: 238.0–239.0° C.) (160.8 mg, yield: 82%).

$^1$H-NMR (CD$_3$OD) (ammonium salt NH$^+$ protons were not observed) δ: 2.72 (s, 6H), 3.82 (s, 6H), 3.93 (s, 12H), 4.09 (s, 8H), 6.89 (s, 4H), 7.44 (d, J=9.5 Hz, 2H), 8.24 (s, 2H), 8.38 (d, J=9.5 Hz, 2H).

EXAMPLE 56

4,8-Bis[5-(3,4,5-trimethoxyphenyl)-2-pyridyl]-1,4,8-triazabicyclo[4.4.0]decane

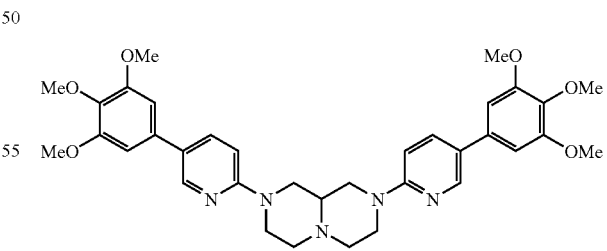

Following the procedure of Example 1, the title compound was obtained as a pale brown amorphous powder (89.9 mg, yield: 71%) from 4,8-bis(5-bromo-2-pyridyl)-1,4,8-triazabicyclo-[4.4.0]decane (91.7 mg, 0.202 mmol) synthesized in a similar manner to that described in Reference Example 1 and 3,4,5-trimethoxyphenylboronic acid (133.3 mg, 0.629 mmol).

¹H-NMR (CDCl₃) δ: 2.37 (br.tt, J=2.3, 12.0 Hz, 1H), 2.43 (ddd, J=3.2, 12.0, 12.0 Hz, 2H), 2.78 (dd, J=12.0, 12.0 Hz, 2H), 2.99 (br.d, J=12.0 Hz, 2H), 3.15 (ddd, J=2.7, 12.0, 12.0 Hz, 2H), 3.88 (s, 6H), 3.92 (s, 12H), 4.25 (br.d, J=12.0 Hz, 2H), 4.33 (br.d, J=12.0 Hz, 2H), 6.70 (s, 4H), 6.74 (d, J=8.8 Hz, 2H), 7.70 (dd, J=2.5, 8.8 Hz, 2H), 8.42 (d, J=2.5 Hz, 2H).

EXAMPLE 57

1,3-Bis[4-[5-(3,4,5-trimethoxyphenyl)-2-pyridyl]-1-piperazinyl]propane

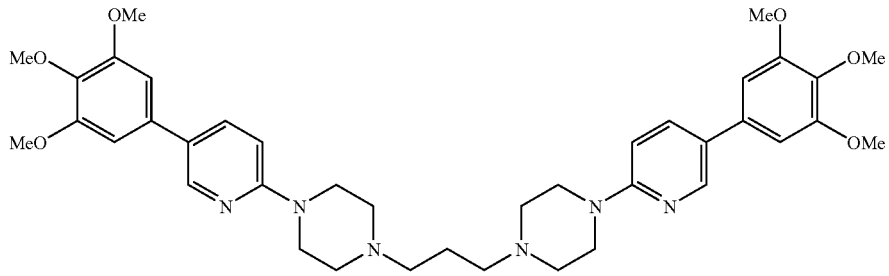

Following the procedure of Example 1, an oil was obtained from 1,3-bis[4-(5-bromo-2-pyridyl)-1-piperazinyl]propane (196.0 mg, 0.370 mmol) synthesized in a similar manner to that described in Reference Example 1 and 3,4,5-trimethoxyphenylboronic acid (244.0 mg, 1.32 mmol). The oil was recrystallized from chloroform-hexane to yield the title compound was obtained as a colorless crystalline powder (melting point: 175.0–176.0° C.) (78.4 mg, yield: 34%).

¹H-NMR (CDCl₃) δ: 1.82 (br.quint, J=7.4 Hz, 2H), 2.48 (br.t, J=7.4 Hz, 4H), 2.61 (br.dd, J=4.7, 4.7 Hz, 8H), 3.62 (br.dd, J=4.7, 4.7 Hz, 8H), 3.88 (s, 6H), 3.91 (s, 12H), 6.70 (s, 4H), 6.72 (d, J=8.9 Hz, 2H), 7.68 (dd, J=2.5, 8.9 Hz, 2H), 8.41 (d, J=2.5 Hz, 2H).

EXAMPLE 58

N,N'-Bis[5-(3,4,5-trimethoxyphenyl)-2-pyridyl]-N,N'-dimethylethylenediamine dimethanesulfonate

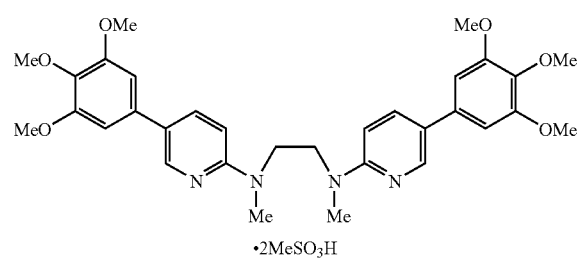

Following the procedure of Example 1, N,N'-bis[5-(3,4,5-trimethoxyphenyl)-2-pyridyl]-N,N'-dimethylethylenediamine was obtained as a pale yellow oil (40.0 mg, yield: 56%) from N,N'-bis(5-bromo-2-pyridyl)-N,N'-dimethylethylenediamine (50.0 mg, 0.120 mmol) synthesized in a similar manner to that described in Reference Example 1 and 3,4,5-trimethoxyphenylboronic acid (79.5 mg, 0.375 mmol).

To a solution of N,N'-bis[5-(3,4,5-trimethoxyphenyl)-2-pyridyl]-N,N'-dimethylethylenediamine (40.0 mg, 0.070 mmol) in methanol (5.0 mL) was added a 1.0 M aqueous methanesulfonic acid (0.14 mL, 0.14 mmol), and the reaction mixture was concentrated under reduced pressure. Ethanol (5.0 mL) was added to the residue, and the mixture was concentrated under reduced pressure. The residue was recrystallized from methanol-diethyl ether to yield the title compound as a pale, yellow crystalline powder (melting point: 204.0–206.0° C.) (32.0 mg, yield: 60%).

¹H-NMR (DMSO-d₆, 120° C.) (ammonium salt NH⁺ protons were not observed) δ: 2.41 (s, 6H), 3.15 (s, 6H), 3.73 (s, 6H), 3.84 (s, 12H), 3.88 (s, 4H), 6.83 (s, 4H), 6.91 (d, J=9.0 Hz, 2H), 7.93 (dd, J=2.4, 9.0 Hz, 2H), 8.30 (d, J=2.4 Hz, 2H).

Test 1 (Evaluation of IgE Antibody Production Inhibiting Activity)

From a mouse (Balb/C, male, 8 weeks old), the spleen was enucleated. The spleen was shredded in 10% FEB/RPMI 1640, and was then disintegrated into single cells through a 70-mesh screen. Those single cells were hemolyzed with Gey's solution, and using RPMI 1640 medium/25 mM HEPES/0.3% BSA, a spleen cell suspension (1×10⁷ cells/mL) was prepared. After an aliquot of the suspension was reacted with a rat anti-mouse Thy-1.2 monoclonal antibody (product of Cedarlane Laboratories Limited) at 4° C. for 1 hour, centrifugation was conducted. Precipitated cells were suspended again (1×10⁷ cells/mL, RPMI/HEPES/BSA). After the suspension was next reacted with a low-cytotoxic rabbit complement (product of Cedarlane Laboratories Limited) at 37° C. for 1 hour, dead cells were removed by specific gravity centrifugation using Lympholyte M (product of Cedarlane Laboratories Limited) so that a B cell fraction was obtained as viable cells.

Using a 96-well plate, the B cells (2×10⁵ cells/0.2 mL/well) were incubated together with LPS (E. coli 026:B6, product of DIFCO Laboratories, Inc.) for 1 day. Mouse IL-4(product of Genzyme Corp.) was then added, followed by further incubation for 6 days.

The IgE antibody production inhibiting activity of each drug was calculated by adding the drug Day 1 of the incubation and assaying the quantity of IgE in the culture supernatant by ELISA after the incubation inhibition activity (IC₅₀) is presented in Table 1.

Further, the solubility (%) of each compound in water was also estimated. The results are presented in Table 1.

TABLE 1

| Compound (Example No.) | IC$_{50}$ (μM) | Water solubility (%) |
|---|---|---|
| 26 | 0.2 | 5 |
| 34 | 0.3 | 5 |
| 35 | 0.2 | 5* |
| 57 | 0.1 | 5* |
| 58 | 0.2 | 5 |

*Solubility in 0.1 M hydrochloric acid

INDUSTRIAL APPLICABILITY

The bis(5-aryl-2-pyridyl) derivatives (1) according to the present invention and salts thereof have excellent IgE antibody production inhibiting activity and are useful as medicinal agents for the prevention or treatment of allergic immune diseases.

Obviously, numerous modifications and variations of the present invention are possible in light of the above teachings. It is therefore to be understood that within the scope of the appended claims, the invention may be practiced otherwise than as specifically described herein.

What is claimed as new and is intended to be secured by letters patent is:

1. A bis(5-aryl-2-pyridyl) compound represented by formula (1) or a salt thereof:

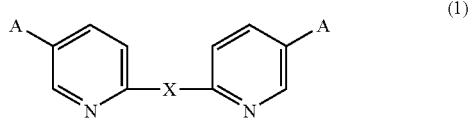

wherein A is a substituted or unsubstituted aromatic hydrocarbon group or a substituted or unsubstituted aromatic heterocyclic group, and X is a group of formula (4):

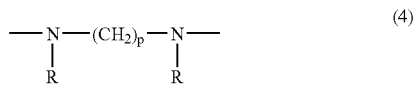

wherein, in formula (4), R is hydrogen or a lower alkyl group and p is an integer of 1 to 6.

2. The bis(5-aryl-2-pyridyl) compound or salt thereof according to claim 1, wherein, A is a substituted or unsubstituted phenyl group, a substituted or unsubstituted pyridyl group, a substituted or unsubstituted thienyl group, a substituted or unsubstituted furyl group, a substituted or unsubstituted benzofuryl group, or a substituted or unsubstituted benzothienyl group.

3. The bis(5-aryl-2-pyridyl) compound or a salt thereof according to claim 2, wherein A is a substituted or unsubstituted phenyl group.

4. The bis(5-aryl-2-pyridyl) compound or a salt thereof according to claim 2, wherein said phenyl group or said pyridyl, thienyl, furyl, benzofuryl or benzothienyl group is substituted by 1 to 3 substituents selected from the group consisting of lower alkyl groups, halogeno(lower alkyl) groups, hydroxy(lower alkyl) groups, lower alkoxy(lower alkyl) groups, lower alkoxy groups, halogen, hydroxy, cyano, (lower alkyl)thio groups, amino, mono- or di-(lower alkyl)amino groups, (lower alkyl)sufonylamino groups, formyl, carboxyl, (lower alkoxy)carbonyl groups, lower alkanoyl groups, pyrrolidinyl, and alkylenedioxy groups.

5. The bis(5-aryl-2-pyridyl) compound or a salt thereof according to claim 1, wherein the lower alkyl group R is methyl, ethyl, n-propyl, isopropyl, n-butyl, isobutyl, sec-butyl, tert-butyl, pentyl, hexyl, cyclopropyl or cyclohexyl.

6. The bis(5-aryl-2-pyridyl) compound or a salt thereof according to claim 2, wherein said phenyl group or said pyridyl, thienyl, furyl, benzofuryl or benzothienyl group is substituted by 1 to 3 substituents selected from the group consisting of methyl, methoxy, ethoxy, n-propoxy, isopropoxy, trifluoroethoxy, methoxyethoxy, hydroxyethoxy, fluorine, chlorine, hydroxy, cyano, methylthio, dimethylamino, pyrrolidinyl, formyl, carboxyl, ethoxycarbonyl, t-butoxycarbonyl, propionyloxy, N-methyl-N-methoxycarbamoyl, acetyl, and methylenedioxy.

7. The bis(5-aryl-2-pyridyl) compound or a salt thereof according to claim 4, wherein said bis(5-aryl-2-pyridyl) compound is N,N'-bis[5-(3,4,5-trimethoxy-phenyl)-2-pyridyl]-N,N'-dimethylethylenediamine dimethanesulfonate.

8. A therapeutic composition having IgE antibody production inhibiting activity, comprising, as an active ingredient, an effective amount of a bis(5-aryl-2-pyridyl) compound or a salt thereof according to claim 1 and a pharmacologically acceptable carrier.

9. A method of treating a subject suffering from an allergic immune disease, which comprises:

administering an effective amount of the bis(5-aryl-2-pyridyl) compound or a salt thereof represented by formula (1)

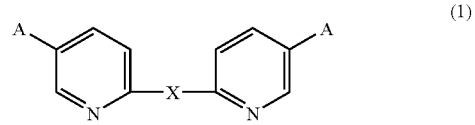

wherein A is a substituted or unsubstituted aromatic hydrocarbon group or a substituted or unsubstituted aromatic heterocyclic group, and X is a group of formula (4):

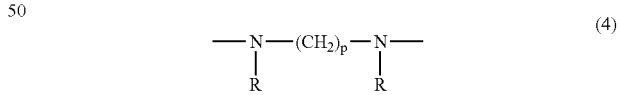

wherein, in formula (4), R is hydrogen or a lower alkyl group and p is an integer of 1 to 6, to said subject.

10. The method according to claim 9, wherein said allergic immune disease is asthma, atopic dermatitis, allergic rhinitis, inflammatory bowel disease, contact dermatitis or an allergic ophthalmopathy.

* * * * *

UNITED STATES PATENT AND TRADEMARK OFFICE
CERTIFICATE OF CORRECTION

PATENT NO. : 7,196,101 B2
APPLICATION NO. : 10/690671
DATED : March 27, 2007
INVENTOR(S) : Hiroyuki Ishiwata et al.

It is certified that error appears in the above-identified patent and that said Letters Patent is hereby corrected as shown below:

Column 50, line 5, " (lower alkyl)sufonylamino groups, "
should read -- (lower alkyl)sulfonylamino groups, --.

Signed and Sealed this

Twelfth Day of June, 2007

JON W. DUDAS
*Director of the United States Patent and Trademark Office*